(12) United States Patent
David et al.

(10) Patent No.: US 7,288,639 B2
(45) Date of Patent: Oct. 30, 2007

(54) DYSSYMMETRICAL DIAZO COMPOUNDS HAVING AT LEAST ONE 4-PYRIDINIUM UNIT AND A CATIONIC OR NON-CATIONIC LINKER, COMPOSITIONS COMPRISING THEM, METHOD OF COLORING, AND DEVICE

(75) Inventors: Hervé David, la Varenne Saint Hilaire (FR); Andrew Greaves, Montevrain (FR); Nicolas Daubresse, la Celles St Cloud (FR)

(73) Assignee: L'Oreal S.A., Paris (FR)

( * ) Notice: Subject to any disclaimer, the term of this patent is extended or adjusted under 35 U.S.C. 154(b) by 48 days.

(21) Appl. No.: 11/300,314

(22) Filed: Dec. 15, 2005

(65) Prior Publication Data

US 2006/0156489 A1 Jul. 20, 2006

Related U.S. Application Data

(60) Provisional application No. 60/645,003, filed on Jan. 21, 2005.

(30) Foreign Application Priority Data

Dec. 15, 2004 (FR) .................................. 04 52998

(51) Int. Cl.
C09B 44/12 (2006.01)
A61Q 5/10 (2006.01)

(52) U.S. Cl. ............................. 534/608; 8/405; 8/426; 8/655

(58) Field of Classification Search ................ 534/608; 8/405, 426, 655
See application file for complete search history.

(56) References Cited

U.S. PATENT DOCUMENTS

| | | | |
|---|---|---|---|
| 3,151,106 A | 9/1964 | Tsang et al. | |
| RE30,199 E | 1/1980 | Rose et al. | |
| 4,557,732 A | 12/1985 | Hähnke et al. | |
| 4,823,985 A | 4/1989 | Grollier et al. | |
| 5,061,289 A | 10/1991 | Clausen et al. | |
| 5,151,106 A | 9/1992 | Bhaumik et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,733,343 A | 3/1998 | Möckli | |
| 5,766,576 A | 6/1998 | Lowe et al. | |
| 5,792,221 A | 8/1998 | Lagrange et al. | |
| 5,852,179 A | 12/1998 | Dado | |
| 5,888,252 A | 3/1999 | Möckli | |
| 6,099,592 A | 8/2000 | Vidal et al. | |
| 6,099,593 A | 8/2000 | Terranova et al. | |
| 6,270,533 B1 | 8/2001 | Genet et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,824,003 B1 | 11/2004 | Wong | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,001,436 B2 | 2/2006 | Vidal et al. | |
| 7,022,143 B2 | 4/2006 | Vidal et al. | |
| 7,166,710 B2 | 1/2007 | Eliu et al. | |
| 2002/0050013 A1 | 5/2002 | Vidal et al. | |
| 2002/0095732 A1 | 7/2002 | Kravtchenko et al. | |
| 2002/0187435 A1 | 12/2002 | Manakli et al. | |
| 2003/0084516 A9 | 5/2003 | Kravtchenko et al. | |
| 2003/0106169 A1 | 6/2003 | Vidal et al. | |
| 2004/0093675 A1 | 5/2004 | Vidal et al. | |
| 2004/0093676 A1 | 5/2004 | Vidal et al. | |
| 2004/0107513 A1 | 6/2004 | Vidal et al. | |
| 2004/0127692 A1 | 7/2004 | David et al. | |
| 2004/0143911 A1 | 7/2004 | Vidal | |
| 2004/0168263 A1 | 9/2004 | Vidal | |
| 2004/0187225 A1 | 9/2004 | Vidal et al. | |
| 2004/0187228 A1 | 9/2004 | Lagrange | |
| 2004/0200009 A1 | 10/2004 | Vidal | |
| 2004/0221399 A1 | 11/2004 | Cotteret et al. | |
| 2004/0244123 A1 | 12/2004 | Vidal et al. | |
| 2004/0244124 A1 | 12/2004 | Plos et al. | |
| 2005/0008594 A1 | 1/2005 | Plos et al. | |
| 2005/0039268 A1 | 2/2005 | Plos et al. | |
| 2006/0149044 A1 | 7/2006 | David et al. | |
| 2006/0174422 A1* | 8/2006 | David et al. .................. 8/401 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 714 954 | 6/1996 |
| EP | 0 770 375 | 5/1997 |
| EP | 1 377 263 | 1/2004 |
| EP | 1 428 505 A1 | 6/2004 |
| EP | 1 433 474 A1 | 6/2004 |
| EP | 1 219 683 B1 | 7/2004 |
| EP | 1 464 327 A1 | 10/2004 |
| FR | 2 586 913 | 3/1987 |

(Continued)

OTHER PUBLICATIONS

English Language Derwent Abstract for DE 23 59 399.

(Continued)

*Primary Examiner*—Fiona T Powers
(74) *Attorney, Agent, or Firm*—Finnegan, Henderson, Farabow, Garrett & Dunner LLP

(57) ABSTRACT

The present disclosure relates to dissymmetrical cationic diazo compounds having at least one 4-pyridinium unit and a cationic or non-cationic linker. The disclosure further relates to dyeing compositions comprising these compounds as a direct dye in a medium appropriate for the dyeing of keratin fibers. Further, the disclosure relates to a method of coloring keratin fibers that employs this composition, and a device having a plurality of compartments.

35 Claims, No Drawings

FOREIGN PATENT DOCUMENTS

| | | |
|---|---|---|
| FR | 2 692 572 | 12/1993 |
| FR | 2 733 749 | 11/1996 |
| FR | 2 750 048 | 12/1997 |
| FR | 2 807 650 | 10/2001 |
| FR | 2 822 693 | 10/2002 |
| FR | 2 822 694 | 10/2002 |
| FR | 2 822 696 | 10/2002 |
| FR | 2 822 698 | 10/2002 |
| FR | 2 825 625 | 12/2002 |
| FR | 2 825 702 | 12/2002 |
| FR | 2 829 926 | 3/2003 |
| FR | 2 844 269 | 3/2004 |
| GB | 1 026 978 | 4/1966 |
| GB | 1 153 196 | 5/1969 |
| JP | 02 19576 | 1/1990 |
| JP | 88 169571 | 1/1990 |
| JP | 05 163124 | 6/1993 |
| JP | 2526099 | 8/1996 |
| WO | WO94/08969 | 4/1994 |
| WO | WO94/08970 | 4/1994 |
| WO | WO95/01772 | 1/1995 |
| WO | WO95/15144 | 6/1995 |
| WO | WO96/15765 | 5/1996 |
| WO | WO99/03834 A2 | 1/1999 |
| WO | WO 02/30374 A1 | 4/2002 |
| WO | WO 02/078596 | 10/2002 |
| WO | WO 02/078596 A2 | 10/2002 |
| WO | WO 02/078660 | 10/2002 |
| WO | WO 02/080869 A2 | 10/2002 |
| WO | WO 02/100366 A2 | 12/2002 |
| WO | WO 02/100368 | 12/2002 |
| WO | WO 02/100369 | 12/2002 |
| WO | WO 02/100834 | 12/2002 |
| WO | WO 04/083312 A2 | 9/2004 |

OTHER PUBLICATIONS

English Language Derwent Abstract for EP 0 770 375.
English Language Derwent Abstract for JP 05 163124.
English Language Derwent Abstract for JP 02-019576 and JP 2526099.
French Search Report for French Application No. 04 52998, for U.S. Appl. No. 11/300,314 (the present application), dated Aug. 3, 2005.
Wang et al., "The Preparation of Symmetrical Azobenzenes from Anilines by Phase Transfer Catalyst Method," Synthetic Communications, vol. 29, No. 13, pp. 2271-2276 (1999).
Onyido et al., "Heteroaromatic Azo-Activated Nucleophilic Substitutions. The Reaction of 4-(p-Methoxyphenylazo)pyridinium Methiodide with Piperidine in Dimethyl Sulphoxide," Heterocycles, vol. 26, No. 2, pp. 313-317 (1987).
Habibi et al., "Efficient Catalytic Oxidation of Primary Aromatic Amines to Azo Derivates by Manganese (III) Tetraphenylporphyrin," J. Chem. Research, vol. 10, pp. 648-649 (1998).
Buncel et al., "Investigations of the Protonation and Tautomeric Equilibria of 4-(p'-Hydroxyphenylazo)pyridine and Related Substrates," Tetrahedron, vol. 39, No. 7, pp. 1091-1101 (1983).
French Search Report for French Patent Appl. No. FR 04/52999, priority document for co-pending appl. No. 11/300,271, Aug. 1, 2005.
French Search Report for French Patent Appl. No. FR 04/53000, priority document for co-pending appl. No. 11/300,284, Aug. 3, 2005.
French Search Report for French Patent Appl. No. FR 04/53002, priority document for co-pending appl. No. 11/300,300, Sep. 16, 2005.
French Search Report for French Patent Appl. No. FR 04/53006, priority document for co-pending appl. No. 11/300,432, Sep. 19, 2005.
French Search Report for French Patent Appl. No. FR 04/53008, priority document for co-pending appl. No. 11/300,303, Aug. 24, 2005.
French Search Report for French Patent Appl. No. FR 04/53005, priority document for co-pending appl. No. 11/300,512, Aug. 23, 2005.
Co-pending U.S. Appl. No. 11/300,284, filed Dec. 15, 2005, by inventors David et al.
Co-pending U.S. Appl. No. 11/300,284, filed Dec. 15, 2005, by inventors David et al.
Co-pending U.S. Appl. No. 11/300,300, filed Dec. 15, 2005, by inventors David et al.
Co-pending U.S. Appl. No. 11/300,432, filed Dec. 15, 2005, by inventors David et al.
Co-pending U.S. Appl. No. 11/300,303, filed Dec. 15, 2005, by inventors David et al.
Co-pending U.S. Appl. No. 11/300,512, filed Dec. 15, 2005, by inventors David et al.
Co-pending U.S. Appl. No. 11/300,271, filed Dec. 15, 2005, by inventors David et al.

* cited by examiner

DYSSYMMETRICAL DIAZO COMPOUNDS HAVING AT LEAST ONE 4-PYRIDINIUM UNIT AND A CATIONIC OR NON-CATIONIC LINKER, COMPOSITIONS COMPRISING THEM, METHOD OF COLORING, AND DEVICE

This application claims benefit of U.S. Provisional Application No. 60/645,003, filed Jan. 21, 2005, the contents of which are incorporated herein by reference. This application also claims benefit of priority under 35 U.S.C. § 119 to French Patent Application No. 04 52988, filed Dec. 15, 2004, the contents of which are also incorporated herein by reference.

The present disclosure relates to dissymmetrical cationic diazo compounds having at least one 4-pyridinium unit and a cationic or non-cationic linker, dyeing compositions comprising these compounds as a direct dye in a medium appropriate for the dyeing of keratin fibers, a method of coloring keratin fibers using this composition, and a device having a plurality of compartments.

Dyeing keratin fibers, such as human hair, with dyeing compositions containing direct dye(s) is known. Direct dyes are colored and/or coloring molecules that have an affinity for the fibers. Direct dyes which are suitable for this purpose include, for example, nitrobenzene, anthraquinone, nitropyridine, azo, xanthene, acridine, azine, or traryamine type direct dyes.

Typically, the direct dye is applied to the fibers for a specific period of time (the leave-in time). The fibers are then rinsed, optionally washed, and dried. The direct dye may be applied to the fibers in the presence of an oxidizing agent if a simultaneous fiber lightening effect is desired.

The colorations which results from the use of direct dyes are temporary or sem-permanent colorations, because the nature of the interactions which bind direct dyes to keratin fibers, and the desorption of the dyes from the surface and/or the core of the keratin fiber, are respsonsible for the relatively low tinctorial strength, and relative poor wash and/or perspiration resistance.

European patent application EP 1377263 discloses specific direct cationic diazo dyes containing two cationic heterocyclic groups. Although these compounds represent an advance in the art, they exhibit dyeing results that are still capable of improvement.

For the purpose of the present disclosure, and in the absence of any indication otherwise:

An alkyl(ene) radical or the alkyl(ene) moiety of a radical is linear or branched.

An alkyl(ene) radical or the alkyl(ene) moiety of a radical is said to be substituted when it comprises at least one substituent chosen from the following groups:

hydroxyl;

$C_1$-$C_4$ alkoxy, $C_2$-$C_4$ (poly)hydroxyalkoxy;

amino, amino substituted by one or two identical or different $C_1$-$C_4$ alkyl groups which optionally carry at least one hydroxyl or $C_1$-$C_2$ alkoxy group, it being possible for said alkyl radicals to form, with the nitrogen atom to which they are attached, a heterocycle containing 5 or 7 ring members which is saturated or unsaturated, is optionally aromatic, is optionally substituted and optionally contains at least one other heteroatom chosen from nitrogen or another heteroatom;

an alkylcarbonylamino radical (R'CO—NR—) in which the radical R is chosen from a hydrogen atom and a $C_1$-$C_4$ alkyl radical;

an alkylsulphonyl radical (R—$SO_2$—) in which the radical R is a $C_1$-$C_4$ alkyl radical;

an alkylsulphinyl radical (R—SO—) in which the radical R is a $C_1$-$C_4$ alkyl radical; and an alkylcarbonyl radical (R—CO—) in which the radical R is a $C_1$-$C_4$ alkyl radical.

An aromatic or non-aromatic, saturated or unsaturated (hetero)cyclic radical, or the aromatic or non-aromatic, saturated or unsaturated (hetero)cyclic moiety of a radical, is said to be substituted when it comprises at least one substituent, for example carried by a carbon atom, chosen from:

an optionally substituted $C_1$-$C_{16}$ alkyl radical, such as, for example, a $C_1$-$C_8$ alkyl radical;

a halogen atom such as, for example, chlorine, fluorine or bromine;

a hydroxyl group;

a $C_1$-$C_4$ alkoxy radical; a $C_2$-$C_4$ (poly)hydroxyalkoxy radical;

an amino radical;

an amino radical substituted by one or two identical or different $C_1$-$C_4$ alkyl radicals which optionally carry at least one hydroxyl or amino or $C_1$-$C_4$ (mono- or di-)alkylamino or $C_1$-$C_2$ alkoxy group, it being possible for the two alkyl radicals, with the nitrogen atom to which they are attached, to form a heterocycle containing 1 to 3 heteroatoms, such as, for example, 1 or 2 heteroatoms, chosen from N, O and S, such as, for example, N, the heterocycle containing 5 to 7 ring members, being saturated or unsaturated and aromatic or non-aromatic, and optionally being substituted;

an alkylcarbonylamino radical (R'CO—NR—) in which the radical R is chosen from a hydrogen atom and a $C_1$-$C_4$ alkyl radical and the radical R' is a $C_1$-$C_2$ alkyl radical;

an aminocarbonyl radical (($R)_2$N—CO—) in which the radicals R, which are identical or different, are chosen from a hydrogen atom and $C_1$-$C_4$ alkyl radicals;

an alkylsulphonylamino or arylsulphonylamino radical (R'$SO_2$—NR—) in which the radical R is chosen from a hydrogen atom and a $C_1$-$C_4$ alkyl radical and the radical R' is chosen from a $C_1$-$C_4$ alkyl radical and a phenyl radical; and an aminosulphonyl radical (($R)_2$N—$SO_2$—) in which the radicals R, which are identical or different, are chosen from a hydrogen atom and $C_1$-$C_4$ alkyl radicals.

The compounds according to the present disclosure are termed "dissymmetrical" when there is no plane of symmetry perpendicular to the linker L. In other words, the two formula members on either side of the linker L are different. More specifically, they are different when their substituents differ in terms of their identities and/or their positions in the molecule.

Where the different groups forming part of the structure of the compounds according to the present disclosure are substituted, the skilled person will select them such that the dissymmetry of the molecule is respected.

One aspect of the present disclosure is to provide direct dyes that do not exhibit one or more of the drawbacks of existing direct dyes.

The present disclosure accordingly provides dissymmetrical cationic diazo compounds represented by formulae (I), (II), and (III) below, their resonance forms, and their acid addition salts and/or their solvates, wherein in the compounds of formulae (I), (II), and (III), the formula members attached to each side of the linker L are either compositionally different or positionally different such that the compounds as a whole are dissymmetrical:

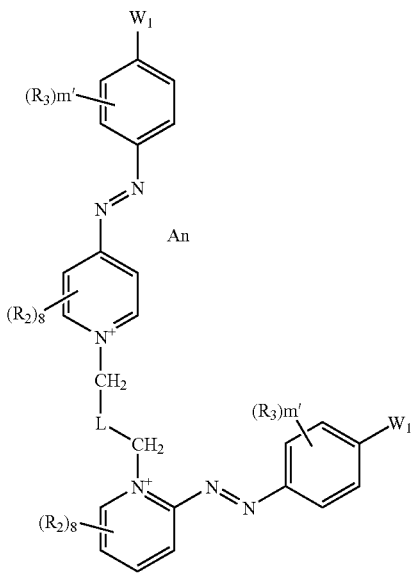
(I)

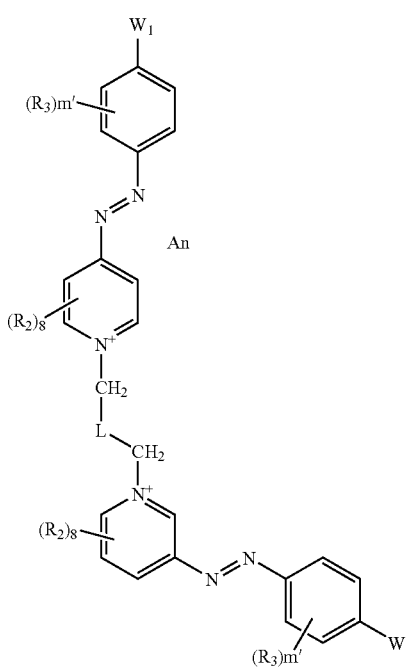
(II)

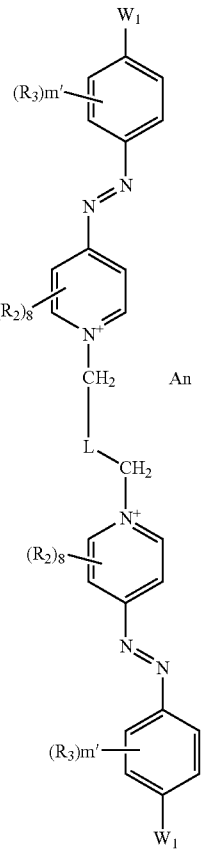
(III)

in which formula:

the radicals $R_2$, which are identical or different, independently of one another may be chosen from:
- optionally substituted $C_1$-$C_{16}$ alkyl radicals optionally interrupted by at least one heteroatom and/or by at least one group containing at least one heteroatom, chosen from, for example, oxygen, nitrogen, sulphur, —CO—, —SO$_2$— or combinations thereof, said alkyl radical being further optionally substituted by at least one group chosen from thio (—SH), $C_1$-$C_4$ thioalkyl; $C_1$-$C_4$ alkylsulphinyl and $C_1$-$C_4$ alkylsulphonyl groups;
- hydroxyl groups,
- $C_1$-$C_4$ alkoxy groups,
- $C_2$-$C_4$ (poly)hydroxyalkoxy groups;
- alkoxycarbonyl groups (RO—CO—) wherein R is a $C_1$-$C_4$ alkyl radical;
- alkylcarbonyloxy radicals (RCO—O—) wherein R is a $C_1$-$C_4$ radical;
- alkylcarbonyl radicals (R—CO—) wherein R is a $C_1$-$C_4$ alkyl radical;
- amino groups;
- amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle containing 1 to 3 heteroatoms, such as, for example, 1 to 2 heteroatoms, chosen from N, O and S, such as, for example, N, and containing 5 to 7 ring members, wherein said heterocycle is saturated or unsaturated, aromatic or non-aromatic and is optionally substituted;

alkylcarbonylamino groups (RCO—NR'—) wherein the radical R is a $C_1$-$C_4$ alkyl radical and the radical R' is chosen from hydrogen and a $C_1$-$C_4$ alkyl radical;

aminocarbonyl groups ($(R)_2$N—CO—) wherein the radicals R independently of one another are chosen from a hydrogen atom and a $C_1$-$C_4$ alkyl radical;

ureido groups (N$(R)_2$—CO—NR'—) wherein the radicals R and R' independently of one another are chosen from a hydrogen atom and a $C_1$-$C_4$ alkyl radical;

aminosulphonyl groups ($(R)_2$N—$SO_2$—) wherein the radicals R independently of one another are chosen from a hydrogen atom and a $C_1$-$C_4$ alkyl radical;

alkylsulphonylamino groups ($RSO_2$—NR'—) wherein R is a $C_1$-$C_4$ alkyl radical and R' is chosen from a hydrogen atom and a $C_1$-$C_4$ alkyl radical;

optionally substituted aryl radicals;

optionally substituted ($C_1$-$C_4$ alkyl)aryl radicals;

alkylsulphinyl groups (R—SO—) wherein R is a $C_1$-$C_4$ alkyl radical;

alkylsulphonyl groups (R—$SO_2$—) wherein R is a $C_1$-$C_4$ alkyl radical;

nitro groups;

cyano groups;

halogen atoms, such as, for example, chlorine or fluorine;

thio groups (HS—);

alkylthio groups (RS—) wherein the radical R is an optionally substituted $C_1$-$C_4$ alkyl radical;

when e is 2, for each of the formulae (I), (II), and (III), two radicals $R_2$ may optionally form, with the carbon atoms to which they are attached, a secondary ring, aromatic or non-aromatic, containing 5 or 6 ring members, such as, for example, 6 members, which is optionally substituted by one or more identical or different groups chosen from hydroxyl, $C_1$-$C_4$ alkyl, $C_1$-$C_4$ alkoxy, $C_2$-$C_4$ (poly)hydroxyalkoxy, amino, and amino substituted by one or two identical or different $C_1$-$C_4$ alkyl radicals which optionally carry at least one hydroxyl group;

e is an integer ranging from 0 to 4; when e is less than 4, the unsubstituted carbon atom(s) of the heterocycle of the formulae (I), (II), and (III) carry a hydrogen atom, the radicals $R_3$, from the formulae (I), (II), and (III), which are identical or different, independently of one another may be chosen from:

optionally substituted $C_1$-$C_{16}$ alkyl radicals optionally interrupted by at least one heteroatom or by at least one group containing at least one heteroatom chosen from, for example, oxygen, nitrogen, sulphur, —CO—, —$SO_2$— or combinations thereof;

hydroxyl groups;

$C_1$-$C_4$ alkoxy groups;

$C_2$-$C_4$ (poly)hydroxyalkoxy groups;

alkoxycarbonyl groups (RO—CO—) wherein R is a $C_1$-$C_4$ alkyl radical;

alkylcarbonyloxy groups (RCO—O—) wherein R is a $C_1$-$C_4$ alkyl radical;

alkylcarbonyl groups (R—CO—) wherein R is a $C_1$-$C_4$ alkyl radical;

amino groups;

amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle containing 1 to 3 heteroatoms, such as, for example, 1 to 2 heteroatoms, chosen from N, O and S, such as, for example, N, and containing 5 to 7 ring members, which is saturated or unsaturated, aromatic or non-aromatic and is optionally substituted;

alkylcarbonylamino groups (RCO—NR'—) wherein the radical R is a $C_1$-$C_4$ alkyl radical and the radical R' is chosen from a hydrogen atom and a $C_1$-$C_4$ alkyl radical;

aminocarbonyl groups ($(R)_2$N—CO—) wherein the radicals R independently of one another are chosen from a hydrogen atom and a $C_1$-$C_4$ alkyl radical;

ureido groups (N$(R)_2$—CO—NR'—) wherein the radicals R and R' independently of one another are chosen from a hydrogen atom and a $C_1$-$C_4$ alkyl radical;

aminosulphonyl groups ($(R)_2$N—$SO_2$—) wherein the radicals R independently of one another are chosen from a hydrogen atom and a $C_1$-$C_4$ alkyl radical;

alkylsulphonylamino groups ($RSO_2$—NR'—) wherein the radicals R and R' independently of one another are chosen from a hydrogen atom and a $C_1$-$C_4$ alkyl radical;

thio groups (HS—);

alkylthio groups (RS—) wherein the radical R is a $C_1$-$C_4$ alkyl radical;

alkylsulphinyl groups (R—SO—) wherein R is a $C_1$-$C_4$ alkyl radical;

alkylsulphonyl groups (R—$SO_2$—) wherein R is a $C_1$-$C_4$ alkyl radical;

nitro groups;

cyano groups;

halogen atoms, such as, for example, chlorine or fluorine;

when m' is greater than or equal to 2, two adjacent radicals $R_3$ may form, with the carbon atoms to which they are attached, a secondary ring, aromatic or non-aromatic containing 6 ring members, which is optionally substituted by one or more identical or different groups chosen from the following groups: hydroxyl, $C_1$-$C_4$ alkyl, $C_1$-$C_4$ alkoxy, $C_2$-$C_4$ (poly)hydroxyalkoxy, amino, and amino substituted by one or two identical or different $C_1$-$C_4$ alkyl radicals which optionally carry at least one hydroxyl group, m' is an integer ranging from 0 to 4; when m' is less than 4, then the unsubstituted carbon atom(s) of the aromatic ring of the formulae (I), (II), and (III) carry a hydrogen atom; The $W_1$ groups of the formulae (I), (II), and (III), which are identical or different, independently of one another, may be chosen from:

hydrogen atoms;

halogen atoms chosen from bromine, chlorine and fluorine, such as, for example, chlorine and fluorine;

an —$NR_5R_6$, $OR_7$, —$NR_4$—Ph—$NR_5R_6$, —$NR_4$—Ph—$OR_7$, —O—Ph—$OR_7$ or —O—Ph—$NR_5R_6$ group, wherein:

$R_4$ and $R_7$, which are identical or different, may be chosen from a hydrogen atom, an optionally substituted $C_1$-$C_{20}$ alkyl radical, such as, for example, an optionally substituted $C_1$-$C_{16}$, alkyl radical, an optionally substituted $C_1$-$C_3$ aralkyl radical and an optionally substituted phenyl radical;

$R_5$ and $R_6$, which are identical or different, may be chosen from a hydrogen atom, an optionally substituted $C_1$-$C_{20}$ alkyl radical, such as, for example, an optionally substituted $C_1$-$C_{16}$, alkyl radical, an optionally substituted phenyl radical, an optionally substituted $C_1$-$C_3$ aralkyl radical and an alkylcarbonyl radical (R—CO—) wherein R is a $C_1$-$C_4$ alkyl radical;

$R_5$ and $R_6$ may optionally form, with the nitrogen atom to which they are attached, a heterocycle containing 1 to 3 heteroatoms, such as, for example, 1 or 2 heteroatoms, chosen from N, O and S, such as, for example, N, and containing 5 to 7 ring members, which is saturated or unsaturated, aromatic or non-aromatic and is optionally substituted;

$R_5$ and $R_6$ may optionally form, with the carbon atom of the aromatic ring adjacent to that to which —$NR_5R_6$ is attached, a 5- or 6-membered saturated heterocycle; and Ph is an optionally substituted phenyl radical;

L is a cationic or non-cationic linker; and

An is chosen from cosmetically acceptable anions, such that the electroneutrality of the compounds of formula (I), (II) and (III) is maintained.

The present disclosure further provides dyeing compositions comprising compounds of formula (I), (II) and/or (III) above, or the acid-addition salts thereof, as direct dyes in a medium appropriate for the dyeing of keratin fibers.

In addition, the present disclosure further provides a method of coloring keratin fibers which comprises contacting keratin fibers with a composition according to the disclosure for a time sufficient to give a desired effect, e.g., desired color. Said fibers may be wet or dry.

Finally, the present disclosure provides a device having a plurality of compartments, i.e., a multi-compartment device. A first compartment of the device contains the composition according to the present disclosure. A second compartment comprises an oxidizing composition.

it has been found that compounds defined above exhibit effective resistance to external agents such as, for example, shampoos, even when the keratin fiber is sensitized. Furthermore, these compounds exhibit improved dyeing properties, such as improved chromaticity and/or coloring power. The compounds may also exhibit low selectivity, meaning that these compounds impart a more uniform coloration between the end and the root of the hair.

Other characteristics and advantages of the disclosure will become apparent upon reading the following description and examples.

In the text below, and in the absence of any indication otherwise, the end-points delimiting a range of values are included in that range.

As indicated above, the disclosure first provides compounds corresponding to the aforementioned formula (I), (II) and (III), resonance forms, acid addition salts, solvates, and mixtures thereof.

In a non-limiting embodiment of the present disclosure, radicals $R_2$ of formula (I), (II), and/or (III) above, which may be identical or different, are chosen from:

halogen atoms chosen from chlorine and fluorine;

$C_1$-$C_4$ alkyl radicals optionally substituted by one or more identical or different radicals chosen from hydroxyl, $C_1$-$C_2$ alkoxy, $C_2$-$C_4$ (poly)hydroxyalkoxy, amino, $C_1$-$C_2$ (di)alkylamino, thio (—SH), $C_1$-$C_4$ alkylsulphinyl, $C_1$-$C_4$ alkylsulphonyl and $C_1$-$C_4$ thioalkyl radicals;

phenyl radicals optionally substituted by at least one identical or different radicals chosen from hydroxyl, $C_1$-$C_2$ alkoxy, $C_2$-$C_4$ (poly)hydroxyalkoxy, amino and $C_1$-$C_2$ (di)alkylamino radicals and a halogen atom such as, for example, chlorine or fluorine;

$C_1$-$C_4$ alkoxy radicals;

$C_1$-$C_4$ alkylsulphonylamino radicals;

$C_2$-$C_4$ (poly)hydroxyalkoxy radicals;

amino radicals;

$C_1$-$C_2$ (di)alkylamino radicals;

$C_2$-$C_4$ (poly)hydroxyalkylamino radicals;

alkylsulphonylamino radicals ($RSO_2N$—) wherein the radical R is $C_1$-$C_4$ alkyl radical;

aminosulphonyl radicals (($R)_2NSO_2$—) wherein the radicals R independently of one another are chosen from a hydrogen atom and a $C_1$-$C_4$ alkyl radical;

alkylthio radicals (RS—) wherein the radical R is a $C_1$-$C_4$ alkyl radical;

alkylsulphinyl radicals (RSO—) wherein the radical R is a $C_1$-$C_4$ alkyl radical;

alkylsulphonyl radicals (R—$SO_2$—) wherein the radical R is a $C_1$-$C_4$ alkyl radical;

alkylcarbonylamino radicals (RCONR'—) wherein the radical R is chosen from a hydrogen atom and a $C_1$-$C_4$ alkyl radical and the radical R' is chosen from a hydrogen atom and a $C_1$-$C_4$ alkyl radical.

In a further non-limiting embodiment of the present disclosure, radicals $R_2$, which may be identical or different, are chosen from methyl, ethyl, 2-hydroxyethyl, 2-methoxyethyl, methylsulphonyl ($CH_3SO_2$—), methylcarbonylamino ($CH_3CONH$—), hydroxyl, amino, methylamino, dimethylamino, 2-hydroxyethylamino, methoxy, ethoxy and phenyl radicals.

In another non-limiting embodiment of the present disclosure, radicals $R_2$ in formula (I), (II) and (III) may form, together with the carbon atoms to which they are attached, a secondary, 6-membered aromatic ring that is optionally substituted with at least one identical or different substituent chosen from hydroxyl, $C_1$-$C_4$ alkyl, $C_1$-$C_4$ alkoxy, amino, and amino substituted by one or two identical or different $C_1$-$C_4$ alkyls that optionally carry at least one hydroxyl or methylcarbonylamino group.

In accordance with this embodiment, the two radicals $R_2$ may optionally form, together with the carbon atoms to which they are attached, a secondary, 6-membered aromatic ring that is optionally substituted with at least one substituent chosen from hydroxyl, methoxy, ethoxy, amino, 2-hydroxyethylamino, dimethylamino and/or (di)-2-hydroxyethylamino substituents.

In at least one embodiment of the present disclosure, the coefficient e is 0.

Radicals $R_3$ of the formula (I), (II) and (III), which may be identical or different, are chosen from, for example,:

optionally substituted $C_1$-$C_{16}$ alkyl radicals, for example, an optionally substituted $C_1$-$C_8$ alkyl radical;

halogen atoms such as chlorine or fluorine;

hydroxyl groups;

$C_1$-$C_2$ alkoxy radicals;

$C_2$-$C_4$ (poly)hydroxyalkoxy radicals;

amino radicals;

amino radicals substituted by one or two identical or different $C_1$-$C_4$ alkyl radicals that optionally carry at least one identical or different substituent chosen from hydroxyl and $C_1$-$C_4$ alkoxy, it being possible for the two alkyl radicals to form, with the nitrogen to which they are attached, a heterocycle containing 1 to 3 heteroatoms, such as, for example, 1 or 2 heteroatoms, chosen from N, O and S, such as, for example, N, the heterocycle containing 5 to 7 ring members, being saturated or unsaturated, aromatic or non-aromatic, and being optionally substituted;

alkylcarbonylamino radicals (RCO—NR'—) wherein the radical R is a $C_1$-$C_4$ alkyl radical and the radical R' is chosen from a hydrogen and a $C_1$-$C_4$ radical;

alkylsulphonylamino radicals (R'SO$_2$—NR—) wherein the radical R is chosen from a hydrogen atom and a C$_1$-C$_4$ alkyl radical and the radical R' is a C$_1$-C$_4$ alkyl radical;

aminosulphonyl radicals ((R)$_2$N—SO$_2$—) wherein the radicals R, which are identical or different, are chosen from a hydrogen atom and a C$_1$-C$_4$ alkyl radical;

alkylthio radicals (RS—) wherein the radical R is a C$_1$-C$_4$ alkyl radical; and alkylsulphonyl radicals (R—SO$_2$—) wherein the radical R is a C$_1$-C$_4$ alkyl radical.

In a further non-limiting embodiment of the present disclosure, radicals R$_3$, which may be identical or different, are chosen from:

a C$_1$-C$_4$ alkyl radical optionally substituted by at least one identical or different radicals chosen from hydroxyl radicals, C$_1$-C$_2$ alkylcarbonylamino radicals, amino radicals substituted by two identical or different C$_1$-C$_2$ alkyl radicals which optionally carry one or more identical or different groups chosen from hydroxyl or C$_1$-C$_2$ alkoxy, it being possible for these two alkyl radicals optionally to form, with the nitrogen atom to which they are attached, a 5- or 6-membered heterocycle which is saturated or unsaturated and is optionally aromatic, chosen from, for example, pyrrolidine, piperazine, homopiperazine, pyrrole, imidazole and pyrazole;

C$_2$-C$_4$ hydroxyalkoxy radicals;

halogen atoms chosen from chlorine and fluorine;

amino radicals;

amino radicals substituted by one or two identical or different C$_1$-C$_2$ alkyl radicals which optionally carry at least one hydroxyl group;

methylcarbonylamino radicals;

methylsulphonylamino radicals;

hydroxyl radicals;

C$_1$-C$_2$ alkoxy radicals;

methylsulphonyl radicals.

According to this embodiment of the present disclosure, radicals R$_3$, which may be identical or different, are chosen from:

methyl, ethyl, propyl, 2-hydroxyethyl, methoxy, ethoxy, 2-hydroxyethyloxy, 3-hydroxypropyloxy and 2-methoxyethyl radicals;

methylsulphonylamino radicals;

amino, methylamino, dimethylamino and 2-hydroxyethylamino radicals;

methylcarbonylamino radicals;

hydroxyl radicals;

chlorine atoms; and methylsulphonyl radicals.

According to another non-limiting embodiment of the present disclosure, when the coefficient m' is greater than or equal to 2, then two adjacent radicals R$_3$ may form, together with the carbon atoms to which they are attached, a secondary, 6-membered aromatic ring that is optionally substituted with at least one identical or different substituent chosen from —NR$_4$—Ph, —NR$_4$—Ph—NR$_5$R$_6$, —NR$_4$—Ph—OR$_7$, hydroxyl, C$_1$-C$_4$ alkyl, C$_1$-C$_4$ alkoxy, C$_2$-C$_4$ (poly)hydroxyalkoxy, C$_1$-C$_4$ alkylcarbonylamino, amino, and amino groups substituted by one or two identical or different C$_1$-C$_4$ alkyl radicals that optionally comprise at least one hydroxyl group.

According to this embodiment, R$_3$ may form, together with the carbon atoms to which they are attached, a secondary, 6-membered aromatic ring that is optionally substituted with at least one substituent chosen from hydroxyl, methoxy, ethoxy, 2-hydroxyethyloxy, amino, methylcarbonylamino, (di)-2-hydroxyethylamino, —NH—Ph, —NH—Ph—NH$_2$, —NH—Ph—NHCOCH$_3$, —NH—Ph—OH and —NH—Ph—OCH$_3$ groups, in which Ph represents an optionally substituted phenyl radical.

Radicals R$_4$ and R$_7$, which may be identical or different, are chosen from:

hydrogen atoms;

C$_1$-C$_6$ alkyl radicals optionally substituted with at least one identical or different substituent chosen from hydroxyl and C$_1$-C$_2$ alkoxy;

aryl and arylalkyl radicals, such as phenyl or benzyl, wherein the aryl moiety is optionally substituted with at least one identical or different substituent chosen from a chlorine atom, an amino group, a hydroxyl, a C$_1$-C$_2$ alkoxy, and an amino that is mono- or disubstituted by two identical or different C$_1$-C$_4$ alkyl radicals that optionally carry at least one hydroxyl group.

In at least one embodiment of the present disclosure, radicals R$_4$ and R$_7$, which may be identical or different, are chosen from:

hydrogen atoms;

optionally substituted C$_1$-C$_3$ alkyl radicals, such as methyl, ethyl, 2-hydroxyethyl or 2-methoxyethyl;

phenyl radicals optionally substituted with at least one identical or different substituent chosen from hydroxyl, C$_1$-C$_2$ alkoxy, amino, and amino groups substituted by at least one C$_1$-C$_4$ alkyl group that optionally carries at least one hydroxyl group.

In another non-limiting embodiment of the present disclosure, radicals R$_4$ and R$_7$, which may be the same or different, are chosen from:

hydrogen;

methyl, and 2-hydroxyl radicals;

phenyl radicals optionally substituted with at least one identical or different substituent chosen from hydroxyl, methoxy, amino, (di)methylamino and (di)(2-hydroxyethyl)amino radicals.

Radicals R$_5$ and R$_6$, which may be identical or different, may be chosen from:

hydrogen atoms;

alkylcarbonyl radicals of the formula (R—CO—), wherein R is chosen from optionally substituted C$_1$-C$_4$ alkyl radicals, C$_1$-C$_6$ alkyl radicals optionally substituted by at least one identical or different substituent chosen from hydroxyl, C$_1$-C$_2$ alkoxy, amino, and C$_1$-C$_4$ (di)alkylamino groups, wherein said C$_1$-C$_6$ alkyl may further be substituted with at least one substituent chosen from C$_1$-C$_4$ alkylsulphonyl, C$_1$-C$_4$ alkylsulphinyl and C$_1$-C$_4$ alkylcarbonyl radicals; and aryl and arylalkyl radicals, wherein the aryl moiety may be optionally substituted by at least one substituent, such as a chlorine atom, an amino, a hydroxyl, a C$_1$-C$_4$ alkoxy and an amino group that is substituted by one or two identical or different substituents chosen from C$_1$-C$_4$ alkyl radicals that optionally carry at least one hydroxyl.

In at least one non-limiting embodiment of the present disclosure, radicals R$_5$ and R$_6$, which may be the same or different, are chosen from:

hydrogen atoms;

methylcarbonyl, ethylcarbonyl and propylcarbonyl radicals;

optionally substituted C$_1$-C$_3$ alkyl radicals, such as methyl, ethyl, 2-hydroxyethyl or 2-methoxyethyl; and phenyl radicals optionally substituted with at least one identical or different substituent chosen from hydroxyl, $C_1$-$C_2$ alkoxy, amino, and amino groups substituted by at least one $C_1$-$C_4$ alkyl radical that optionally carries at least one hydroxyl group.

In a further non-limiting embodiment of the present disclosure, radicals $R_5$ and $R_6$, which may be the same or different, are chosen from:

hydrogen atoms;

methyl, ethyl and 2-hydroxyethyl radicals;

methylcarbonyl, ethylcarbonyl and propylcarbonyl radicals;

phenyl radicals optionally substituted by a hydroxyl, methoxy, amino, (di)methylamino or (di)(2-hydroxyethyl)amino radical.

In another non-limiting embodiment of the present disclosure the radicals $R_5$ and $R_6$ may form, together with the nitrogen atom to which each is attached, an optionally saturated, optionally aromatic, optionally substituted heterocycle comprising from 5 to 7 ring members and from 1 to 3 heteroatoms, such as 1 or 2 heteroatoms, chosen from N, O and S. In a non-limiting embodiment, said heteroatom(s) is/are N.

Non-limiting examples of heterocycles comprising from 5 to 7 ring members that are suitable for use in the present disclosure include, but are not limited to: piperidine, 2-(2-hydroxyethylpiperidine), 4-(aminomethyl)piperidine, 4-(2-hydroxyethyl)-piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine, 1-methyl-1,4-perhydrodiazepine, pyrrole, 1,4-dimethylpyrrole, 1-methyl-4-ethylpyrrole, and 1-methyl-4-propylpyrrole.

In a non-limiting embodiment of the present disclosure, the heterocycle comprising from 5 to 7 ring members is chosen from: piperidine, piperazine, homopiperazine, pyrrole, imidazole and pyrazole type heterocycles that are optionally substituted with at least one substituent chosen from methyl, hydroxyl, amino and/or (di)methylamino.

In another non-limiting embodiment of the present disclosure, the radicals $R_5$ and $R_6$ may form, together with with the carbon atom of the aromatic ring optionally substituted by a hydroxyl and adjacent to that to which —$NR_5R_6$ is attached, a 5- or 6-membered saturated heterocycle.

For example, the group —$NR_5R_6$ with the aromatic nucleus optionally substituted by a hydroxyl may correspond to the following compounds:

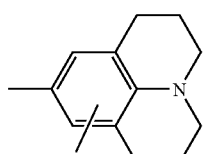

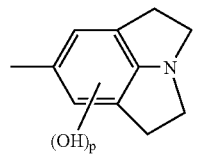

where p = 0 or 1

In a non-limiting embodiment of the present disclosure, L is a non-cationic linker. According to this embodiment, the non-cationic linker L may be chosen from:

a covalent bond;

optionally substituted $C_1$-$C_{40}$ alkyl, for example, a $C_1$-$C_{20}$, radicals that may optionally be interrupted by a saturated or unsaturated, aromatic or non-aromatic heterocycle comprising from 3 to 7 ring members, wherein said heterocycle is optionally substituted and/or optionally fused; said alkyl radical being optionally interrupted by at least one heteroatom and/or at least one group comprising at least one heteroatom, such as oxygen, nitrogen, sulphur, —CO—, —$SO_2$— and combinations thereof; wherein L does not comprise an azo, nitro, nitroso or peroxo bond, and an optionally substituted phenyl radical.

According to another non-limiting embodiment of the present disclosure, linker L is cationic. According to this embodiment, the cationic linker L may be chosen from $C_2$-$C_{40}$ alkyls that carry at least one cationic charge and which are optionally substituted and/or optionally interrupted by at least one saturated or unsaturated, aromatic or non-aromatic, identical or different (hetero)cycle containing from 3 to 7 ring members and/or optionally interrupted by at least one heteroatom and/or at least one group containing at least one heteroatom, such as, for example, oxygen, nitrogen, sulphur, a group —CO— or —$SO_2$— or combinations thereof, wherein the linker L does not comprise an azo, nitro, nitroso or peroxo bond, and wherein the linker L carries at least one cationic charge.

According to at least one embodiment, L is a non-cationic linker. Non-limiting examples of non-cationic linkers that may be utilized in the present disclosure include, but are not limited to alkyl-type linkers, including, but not limited to methylene, ethylene, linear or branched propylene, linear or branched butylene, linear or branched pentylene, and linear or branched hexylene, wherein said alkyl-type linkers may be substituted and/or interrupted as indicated above. In a non-limiting embodiment, when said alkyl-type linkers are substituted with at least one identical or different substituent, the substituent(s) is/are chosen from hydroxyl, $C_1$-$C_2$ alkoxy, $C_1$-$C_2$ dialkylamino, ($C_1$-$C_4$ alkyl)carbonyl and $C_1$-$C_4$ alkyl sulphonyl.

Non-limiting examples of aromatic or non-aromatic, saturated or unsaturated cycle or heterocycle that may interrupt the alkyl portion of linker L include, but are not limited to phenylene, naphthylene, phenanthrylene, triazinyl, pyrimidinyl, pyridinyl, pyridazinyl, quinoxalinyl and cyclohexyl radicals.

Further non-limiting examples of linkers L include, but are not limited to methylene, ethylene, linear or branched propylene, linear or branched butylene, linear or branched pentylene and linear or branched hexylene radicals optionally substituted and/or interrupted as indicated above.

Further non-limiting examples of an aromatic or non-aromatic, saturated or unsaturated cycle or heterocycle that may interrupt the alkyl portion of linker L include, but are not limited to phenylene, naphthylene, phenanthrylene, triazinyl, pyrimidinyl, pyridinyl, pyridazinyl, quinoxalinyl and cyclohexyl radicals.

In a non-limiting embodiment of the present disclosure, the non-cationic linker L is chosen from:

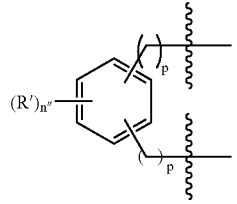 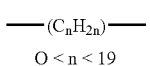

$0 < n < 19$ p is 0 or 1
n″ is an integer between 0 and 4

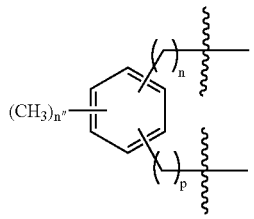

p is 0 or 1
n″ is an integer between 0 and 4

—(C$_n$H$_{2n}$)—X $0 < n < 10$
X = NH, NR$_4$, O
S, SO, SO$_2$

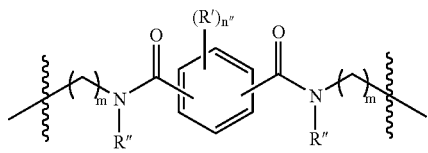

m is an integer between 0 and 6
n″ is an integer between 0 and 4

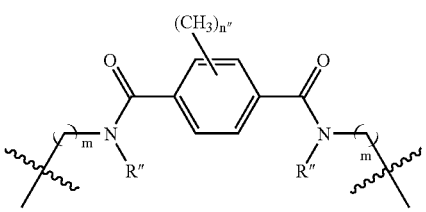

m is an integer between 0 and 6
n″ is an integer between 0 and 4
The aromatic ring positions not substituted by a methyl radical carry a hydrogen atom In another non-limiting embodiment of the present disclosure, linker L is cationic. According to this embodiment, the cationic linker L may be a $C_2$-$C_{20}$ alkyl radical that is:
1—interrupted by at least one group corresponding to the following formulae:

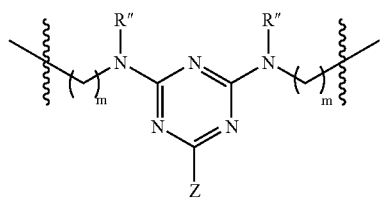

m is an integer between 0 and 6
Z = OH, NR$_8$R$_9$ (a)

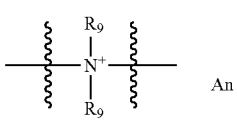

(b)

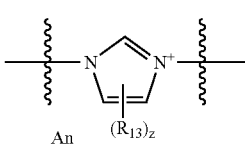

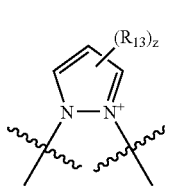

m is an integer between 0 and 6
n‴ is an integer between 0 and 3

(c)

wherein:
R′ has the same definition as R$_3$ above;
Each R″ is identical, and is chosen from hydrogen and $C_1$-$C_4$ alkyls;
R$_8$ and R$_9$, which may be identical or different, are chosen from hydrogen and $C_1$-$C_8$ alkyl radicals that are optionally substituted with at least one identical or different substituent chosen from hydroxyl, $C_1$-$C_2$ alkoxy, $C_2$-$C_4$ (poly)hydroxyalkoxy, amino, $C_1$-$C_2$ (di)alkylamino and optionally substituted aryl.

Further non-limiting examples of non-cationic linker L include, but are not limited to:

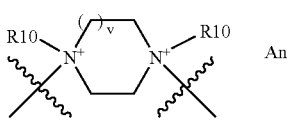

(d)

in which:
R$_9$ and R$_{10}$ independently of one another are chosen from $C_1$-$C_8$ alkyl radicals; $C_1$-$C_6$ monohydroxyalkyl radicals; $C_2$-$C_6$ polyhydroxyalkyl radicals; $C_1$-$C_6$ alkoxy-$C_1$-$C_6$ alkyl radicals; aryl radicals such as phenyl which is optionally substituted; arylalkyl radicals such as benzyl which is optionally substituted; $C_1$-$C_6$ aminoalkyl radicals; $C_1$-$C_6$ aminoalkyl radicals whose amine is substituted by one or two identical or different $C_1$-$C_4$ alkyl radicals; and $C_1$-$C_6$ alkylsulphonyl radicals, two radicals $R_9$ may, together with the nitrogen atom to which they are attached, form a saturated or unsaturated, optionally substituted ring having from 5 to 7 ring members;

$R_{13}$ radicals, which are identical or different, are chosen from halogen atoms chosen from bromine, chlorine and fluorine, $C_1$-$C_6$ alkyl radicals, $C_1$-$C_6$ monohydroxyalkyl radical, a $C_2$-$C_6$ polyhydroxyalkyl radical, a $C_1$-$C_6$ alkoxy radicals, $C_1$-$C_4$ (di)alkylamino radicals, hydroxycarbonyl radicals, $C_1$-$C_6$ alkylcarbonyl radicals, $C_1$-$C_6$ thioalkyl radicals, $C_1$-$C_6$ alkylthio radicals, $C_1$-$C_6$ alkylsulphonyl radicals, optionally substituted benzyl radicals, and phenyl radicals which are optionally substituted by at least one radical chosen from methyl, hydroxyl, amino and methoxy radicals;

An is chosen from organic or inorganic anions and anion mixtures;

z is an integer ranging from 1 to 3, wherein if z is <3, the unsubstituted carbon atoms may carry a hydrogen atom;

v is an integer ranging from 1 to 2, such as 1; and

2—optionally interrupted by at least one heteroatom or group containing at least one heteroatom, and combinations thereof, such as, for example, oxygen, nitrogen, sulphur, a —CO— group or a —$SO_2$— group, with the proviso that linker L does not comprise a nitro, nitroso or peroxo bond or group; and 3—optionally substituted by at least one substituent chosen from hydroxyl, $C_1$-$C_2$ alkoxy, $C_2$-$C_4$ (poly)hydroxyalkoxy, and amino substituted by at least one linear or branched $C_1$-$C_2$ alkyl groups that optionally carry at least one hydroxyl.

In a non-limiting embodiment, $R_9$ and $R_{10}$ of formula (a) and (d), which may be the same or different, are separately chosen from $C_1$-$C_6$ alkyl, $C_1$-$C_4$ monohydroxyalkyl, $C_2$-$C_4$ polyhydroxyalkyl, $C_1$-$C_6$ alkoxy-$C_2$-$C_4$ alkyl, and $C_2$-$C_6$ dimethylaminoalkyl radicals. For example, $R_9$ and $R_{10}$, may independently be chosen from methyl, ethyl and 2-hydroxyethyl radicals.

In a further non-limiting embodiment of the present disclosure, $R_{13}$ in formula (b) and (c) above is chosen from halogen atoms chosen from chlorine and fluorine, $C_1$-$C_6$ alkyl radicals, $C_1$-$C_4$ monohydroxyalkyl radicals, $C_1$-$C_4$ alkoxy radicals, hydroxycarbonyl radicals, $C_1$-$C_6$ alkylthio radicals and amino radicals disubstituted by a $C_1$-$C_4$ alkyl radical.

In yet another non-limiting embodiment of the present disclosure, $R_{13}$ in formula (b) or (c) above is chosen from a chlorine atom, and methyl, ethyl, 2-hydroxyethyl, methoxy, hydroxycarbonyl and dimethylamino radicals.

In a further non-limiting embodiment, z in formula (b) and (c) above is 0.

In the formulae (I), (II) and (III), An represents an organic or inorganic anion or anion mixture. The presence of An allows the charge or charges on the compounds of formula (I), (II) and (III) to be balanced. For example, An may be chosen from halides, such as chloride, bromide, fluoride or iodide; hydroxides; sulphates; hydrogensulphates; alkylsulphates for which the alkyl moiety is linear or branched and is $C_1$-$C_6$, such as methylsulphate or ethylsulphate ion; carbonates; hydrogencarbonates; salts of carboxylic acids, such as formate, acetate, citrate, tartrate and oxalate; alkylsulphonates wherein the alkyl moiety is linear or branched and is $C_1$-$C_6$, such as the methylsulphonate ion; arylsulphonates, including but not limited to those for which the aryl moiety, which may be phenyl, is optionally substituted by at least one $C_1$-$C_4$ substitutents, such as 4-tolylsulphonate; and alkylsulphonyls such as mesylate.

Non-limiting examples of the acid addition salts of the compounds of formula (I), (II) and (III) include the addition salts of these compounds with an organic or inorganic acid, such as hydrochloric acid, hydrobromic acid, sulphuric acid, and/or (alkyl- or phenyl-)sulphonic acids, such as p-toluenesulphonic acid or methylsulphonic acid.

The solvates of compounds of formula (I), (II) and (III) represent the hydrates of these compounds or the combination of at least one of these compounds with a linear or branched $C_1$-$C_4$ alcohol such as methanol, ethanol, isopropanol or n-propanol.

Non-limiting examples of the compounds of formula (I), (II), or (III) include, but are not limited to, those compounds that correspond to formula (I'), (I''), (I'''), (II'), (II''), (II'''), (III'), (III''), (III''') below, as well as the resonance forms, acid addition salts, solvates, and mixtures thereof:

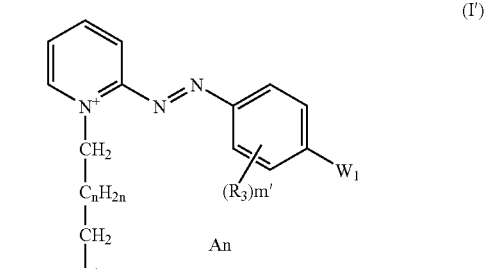

(I')

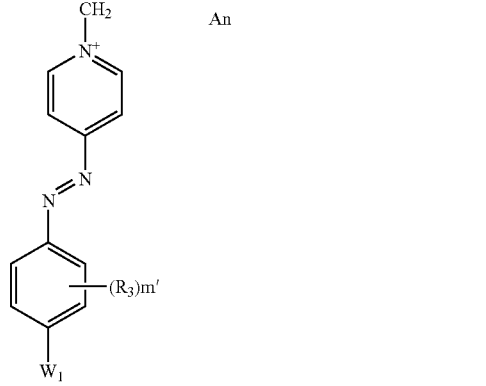

(I'')

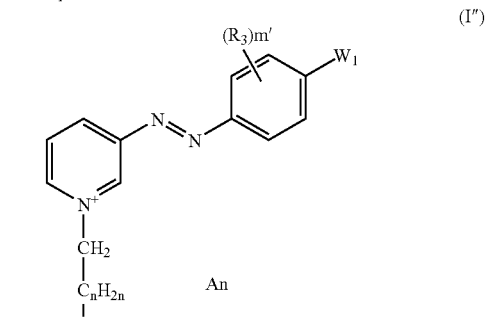

-continued
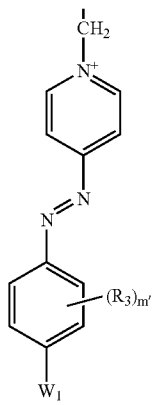
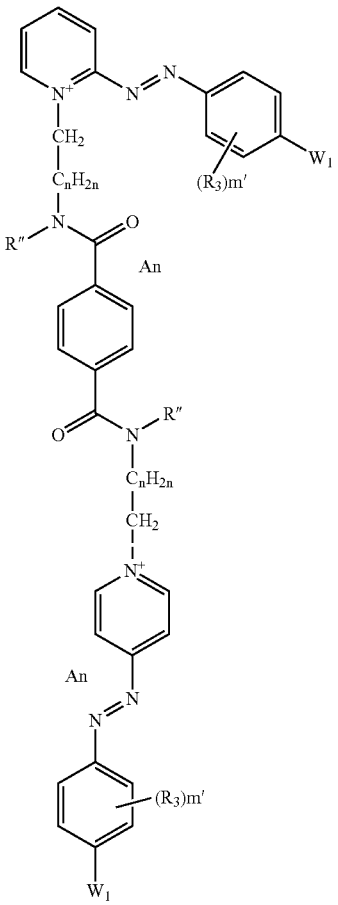
R″ = H, Me
n = integer between 1 and 6
(II′)
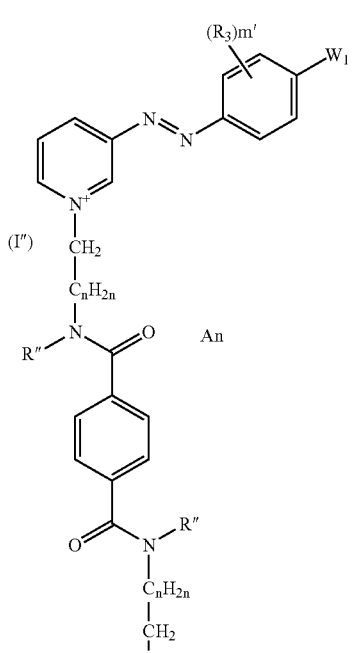
(I‴)
(I″)
(II″)

-continued
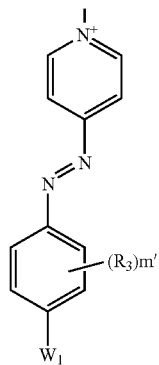
R″ = H, Me
n = integer between 1 and 6
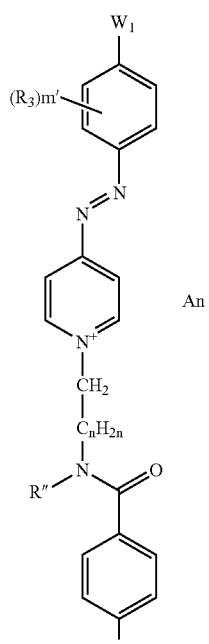
(II‴)
R″ = H, Me
n = integer between 1 and 6
-continued
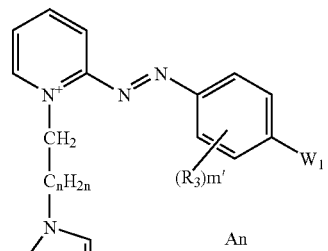
(III′)
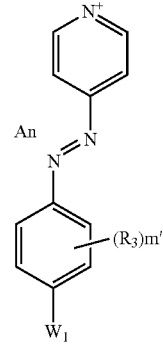
n = integer between 2 and 5
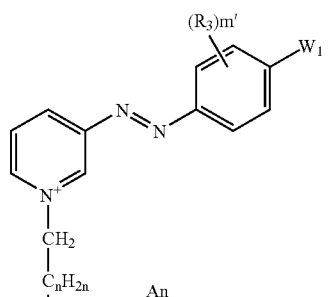
(III″)
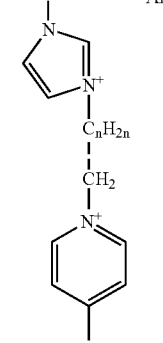
n = integer between 2 and 5

-continued

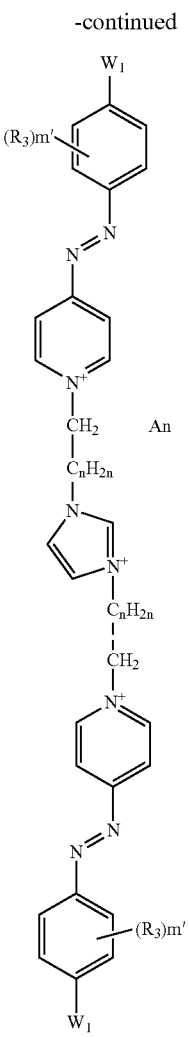

(III''')

n = integer between 2 and 5 wherein $R_3$, $W_1$ and m' are defined as set forth above.

The compounds corresponding to the monoazo species may be obtained, for example, by the preparation processes described in the following documents: U.S. Pat. No. 5,708, 151; J. Chem. Res., Synop. (1998), (10), 648-9; U.S. Pat. Nos. 3,151,106; 5,852,179; Heterocycles, 1987, 26 (2) 313-7, Synth. Commun. 1999, 29 (13), 2271-6, Tetrahedron, 1983, 39 (7), 1091-1101. The compounds of the diazo species may be obtained, for instance, by the synthesis described in European Patent Application No. EP 1 377 263.

The present disclosure further provides a dyeing composition comprising at least one compound of formula (I), (II) and (III), the acid addition salts thereof, the solvates thereof, and/or mixtures thereof, as a direct dye in a medium suitable for dyeing keratin fibers.

in a non-limiting embodiment of the present disclosure, the compound(s) of formula(e) (I), (II) and (III), either individually or as a mixture, may be present in the dyeing composition in an amount ranging from 0.001% to 20% by weight, such as from 0.01% to 10% by weight, more specifically from 0.05% to 5% by weight, relative to the total weight of the dyeing composition.

The dyeing composition according to the disclosure may further comprise at least one oxidation base. This oxidation base may be chosen from the oxidation bases conventionally used in oxidation dyeing, such as para-phenylenediamines, bis(phenyl)alkylenediamines, para-aminophenols, ortho-aminophenols and heterocyclic bases.

Examples of the aforementioned para-phenylenediamines include, but are not limited to para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-amino-phenylpyrrolidine, 2-thienyl-para-phenylenediamine, 2-β-hydroxyethylamino-5-aminotoluene, and the acid addition salts thereof.

In a non-limiting embodiment of the present disclosure, the para-phenylenediamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

Examples of the aforementioned bis(phenyl)alkylenediamines include, but are not limited to: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methyl-aminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

Examples of the aforementioned para-aminophenols include, but are not limited to para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Examples of the aforementioned ortho-aminophenols include, but are not limited to 2-aminophenol, 2-amino-5-methylphenol, 2-amino-6-methylphenol and 5-acetamido-2-aminophenol, and the acid addition salts thereof.

Examples of the aforementioned heterocyclic bases include, but are not limited to pyridine derivatives, pyrimidine derivatives and pyrazole derivatives.

Non-limiting examples of the aforementioned pyridine derivatives include, but are not limited to, those compounds described in British Patents GB 1 026 978 and GB 1 153 196, as well as 2,5-diaminopyridine, 2-(4-methoxyphenyl)amino-3-amino-pyridine, 2,3-diamino-6-methoxypyridine, 2-(β-methoxyethyl)amino-3-amino-6-methoxypyridine and 3,4-diaminopyridine, and the acid addition salts thereof.

Non-limiting examples of the aforementioned pyrimidine derivatives include, but are not limited to the compounds described, for example, in German Patent No. DE 2 359 399; Japanese Patent Nos. JP 88-169 571; JP 05-163 124; European Patent No. EP 0 770 375, or international patent application publication no. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives, such as those mentioned in French patent application FR-A-2 750 048, such as pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo-[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo-[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, the acid addition salts thereof, and the tautomeric forms thereof, when a tautomeric equilibrium exists.

Non-limiting examples of the aforementioned pyrazole derivatives include the compounds described in German Patent Nos. DE 3 843 892 and DE 4 133 957; international patent application publication nos. WO 94/08969 and WO 94/08970; French patent application no. FR-A-2 733 749, and German patent application no. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The dyeing composition of the present disclosure may further contain at least one coupler, such as those conventionally used in the dyeing of keratin fibers. Examples of these couplers include, but are not limited to meta-phenylenediamines, meta-aminophenols, meta-diphenols, naphthalenic couplers and heterocyclic couplers.

Specific, non-limiting examples of the aforementioned couplers include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene and the acid addition salts thereof.

The at least one oxidation base may be present in the dyeing composition in an amount ranging from 0.001% to 10% by weight, for example, from 0.005% to 6% by weight relative to the total weight of the dyeing composition.

The at least one coupler may be present in the dyeing composition in an amount ranging from 0.001% to 10% by weight, for example, from 0.005% to 6% by weight relative to the total weight of the dyeing composition.

In a non-limiting embodiment of the present disclosure, the acid addition salts that may be used in the context of the dyeing compositions of the present disclosure for the oxidation bases and couplers are selected from the aformentioned compounds in the context of the definition of the compounds of formula (I), (II) and (III).

The composition according to the disclosure may further comprise at least one additional direct dye other than the compounds of formula (I), (II) and (III). This at least one additional direct dye may be chosen from cationic and nonionic species.

The at least one additional direct dye may be chosen from, for example, but not limited to, nitrobenzene, azo, azomethine, methine, tetraazapentamethine, anthraquinone, naphthoquinone, benzoquinone, phenothiazine, indigoid, xanthene, phenanthridine and phthalocyanine dyes, dyes derived from triarylmethane, and natural dyes, and mixtures thereof.

For example, the at least one additional direct dye may be chosen from the following red or orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

Further non-limiting examples of the at least one additional direct dye include yellow and green-yellow nitrobenzene direct dyes, such as:
1-β-hydroxyethyloxy-3-methylamino-4-nitrobenzene, 1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Still further non-limiting examples of the at least one additional direct dye include blue or violet nitrobenzene direct dyes, such as:
1-(β-hydroxyethyl)amino-4-N,N-bis(β-hydroxyethyl)amino-2-nitrobenzene,
1-(γ-hydroxypropyl)amino-4-N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines having the following formula:

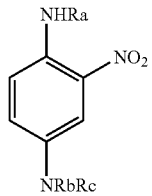

wherein:
Rb is chosen from a $C_1$-$C_4$ alkyl radical, a β-hydroxyethyl radical, a β-hydroxypropyl radical and a γ-hydroxypropyl radical;
Ra and Rc, which may be identical or different, are chosen from β-hydroxyethyl, β-hydroxypropyl, γ-hydroxypropyl and β,γ-dihydroxypropyl radicals, wherein at least one of the radicals Rb, Rc or Ra is a γ-hydroxypropyl and Rb and Rc are not both a β-hydroxyethyl radical when Ra is a γ-hydroxypropyl radical, such as those compounds described in French patent FR 2 692 572.

Non-limiting examples of azo direct dyes that may be used in the present disclosure include the cationic azo dyes described in international patent application nos. WO 95/15144, WO 95/01772, WO 02/078660, WO 02/100834, and WO 02/100369; European Patent No. EP 714954; and French Patent Nos. FR 2 822 696, FR 2 825 702, FR 2 825 625, FR 2 822 698, FR 2 822 693, FR 2 822 694, FR 2 829 926, FR 2 807 650, and FR 2 844 269, such as 1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methylsulphate.

Further non-limiting azo direct dyes that may be utilized in the present disclosure include the following dyes described in the Colour Index International 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Still further non-limiting examples of azo direct dyes that may be utilized in the present disclosure include 1-(4'-aminodiphenylazo)-2-methyl-4-[bis(β-hydroxyethyl)amino]benzene and 4-hydroxy-3-(2-methoxyphenylazo)-1-naphthalenesulphonic acid.

Non-limiting examples of quinone direct dyes that may be utilized in the present disclosure include:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99
1-N-methylmorpholiniumpropylamino-4-hydroxyanthraquinone
1-aminopropylamino4-methylaminoanthra-quinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Non-limiting examples of azine dyes that may be utilized in the present disclosure include:
Basic Blue 17
Basic Red 2.

Non-limiting examples of triarylmethane dyes that may be utilized in the present disclosure include:
Basic Green 1
Acid Blue 9
Basic Violet 3
Basic Violet 14
Basic Blue 7
Acid Violet 49
Basic Blue 26
Acid Blue 7.

Non-limiting indoamine dyes that may be utilized in the present disclosure include:

2-β-hydroxyethylamino-5-[bis(β-4'-hydroxyethyl)amino]anilino-1,4-benzoquinone;

2-β-hydroxyethylamino-5-(2'-methoxy-4'-amino)anilino-1,4-benzoquinone;

3-N-(2'-chloro-4'-hydroxy)phenylacetyl-amino-6-methoxy-1,4-benzoquinoneimine;

3-N-(3'-chloro-4'-methylamino)phenylureido-6-methyl-1,4-benzoquinoneimine;

3-[4'-N-(ethylcarbamylmethyl)amino]phenylureido-6-methyl-1,4-benzoquinoneimine.

Non-limiting examples of tetraazapentamethine type dyes that may be utilized in the present disclosure include the following compounds given in the table below, in which An is defined as above:

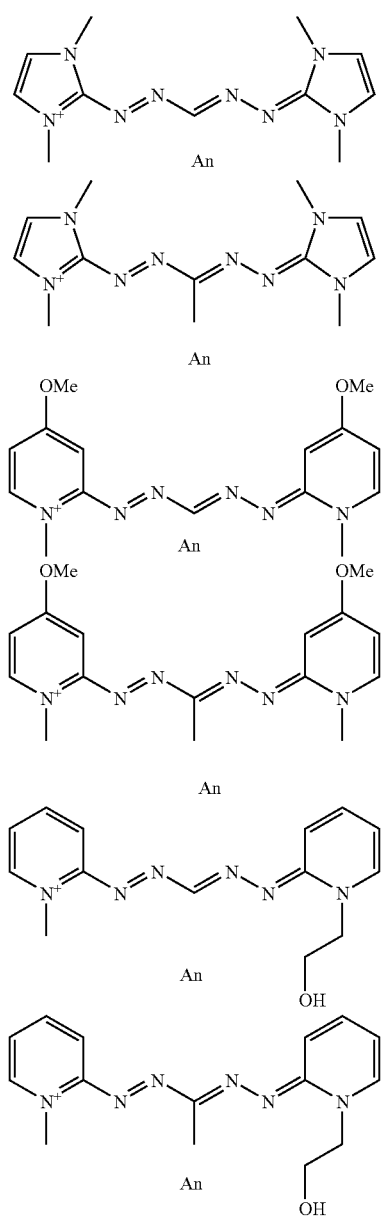

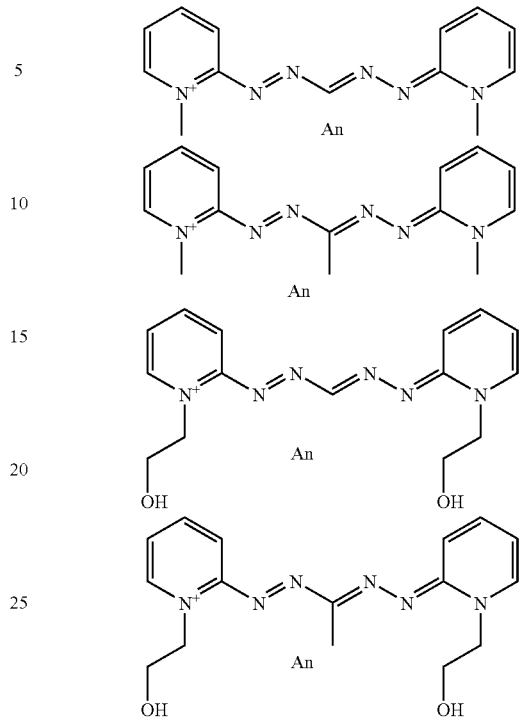

Non-limiting examples of natural direct dyes that may be utilized in the present disclosure include lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, such as henna-based poultices or extracts.

When present, the at least one additional direct dye is present in the dye composition in an amount ranging from 0.001% to 20% by weight, such as 0.01% to 10% by weight, relative to the total weight of the dye composition.

The medium that is suitable for dyeing, also known as the dye vehicle, may be chosen from water or a mixture of water and at least one organic solvent. The organic solvent may be chosen so as to dissolve compounds that are otherwise insufficiently water-soluble.

Non-limiting examples of organic solvents that may be utilized in the present disclosure include: linear or branched, such as saturated monoalcohols or diols containing from 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, such as ethylene glycol monomethyl, monoethyl and monobutyl ether, propylene glycol and its ethers, such as propylene glycol monomethyl ether, butylene glycol and dipropylene glycol; and also diethylene glycol alkyl ethers, for example the $C_1$-$C_4$ ethers such as diethylene glycol monoethyl ether or monobutyl ether, and mixtures thereof.

When present, the solvent is contained in the composition in an amount ranging from 1% to 40% by weight, such as from 5% to 30% by weight, relative to the total weight of the composition.

The dyeing composition in accordance with the disclosure may further include adjuvants that are conventionally used in compositions for dyeing the hair. Non-limiting examples of such adjuvants include anionic, cationic, nonionic, amphoteric or zwitterionic surfactants and mixtures thereof; anionic, cationic, nonionic, amphoteric or zwitterionic polymers and mixtures thereof; mineral or organic thickeners, such as anionic, cationic, nonionic and amphoteric polymeric associative thickeners; antioxidants; penetrants; sequestrants; fragrances; buffers; dispersants; conditioning agents such as silicones, which may or may not be volatile and/or modified; film-forming agents; ceramides; preservatives; and opacifiers.

The adjuvants, when present, are each contained in the composition in an amount ranging from 0.01% to 20% by weight relative to the total weight of the composition.

The person skilled in the art will of course take care to select this or these optional additional compounds such that the advantageous properties intrinsically associated with the oxidation dyeing composition in accordance with the present disclosure are not, or not substantially, adversely affected by the envisaged addition(s).

The pH of the dyeing composition in accordance with the present disclosure may range from 3 to 12, such as, for example, from 5 to 11. The pH may be adjusted to a desired value through the use of acidifying or alkalifying agents usually used in the dyeing of keratin fibers, or alternatively using standard buffer systems.

Non-limiting examples of acidifying agents that may be utilized in the present disclosure include mineral or organic acids such as hydrochloric acid, orthophosphoric acid, sulphuric acid, carboxylic acids such as acetic acid, tartaric acid, citric acid and lactic acid, and sulphonic acids.

Non-limiting examples of alkalifying agents that may be utilized in the present disclosure include aqueous ammonia, alkaline carbonates, alkanolamines such as monoethanolamine, diethanolamine and triethanolamine and derivatives thereof, sodium hydroxide, potassium hydroxide and compounds having the following formula:

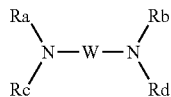

wherein W is a propylene residue that is optionally substituted with a hydroxyl group or a $C_1$-$C_4$ alkyl; Ra, Rb, Rc and Rd, which are identical or different, are chosen from hydrogen atoms, $C_1$-$C_4$ alkyl radicals, and $C_1$-$C_4$ hydroxyalkyl radicals.

The dyeing composition according to the present disclosure may be in various forms, such as in the form of liquids, creams or gels, or in any other form that is suitable for dyeing keratin fibers, such as human hair.

The composition according to the present disclosure may further comprise at least one oxidizing agent. When the composition comprises at least one oxidizing agent, the composition is referred to as a ready-to-use composition.

For the purposes of the present disclosure, a ready-to-use composition is a composition intended to be applied immediately to the keratin fibers, i.e., it may be stored in unmodified form before use or may result from the extemporaneous mixing of two or more compositions.

The composition may also be obtained by mixing the composition with an oxidizing composition.

The at least one oxidizing agent may be any oxidizing agent conventionally used in the field. Thus it may be chosen from hydrogen peroxide, urea peroxide, alkali metal bromates, persalts such as perborates and persulphates, and also enzymes, among which mention may be made of peroxidases, 2-electron oxidoreductases such as uricases, and 4-electron oxygenases, for instance laccases. In at least one embodiment, hydrogen peroxide may be used as the oxidizing agent.

The amount of the at least one oxidizing agent may range from 1% to 40% by weight relative to the total weight of the ready-to-use composition, such as, for example, from 1% to 20% by weight relative to the total weight of the ready-to-use composition.

The oxidizing composition used may be an aqueous composition and may be in the form of a solution or an emulsion.

In at least one embodiment, the composition free of oxidizing agent is mixed with about 0.5 to 10 weight equivalents of the oxidizing composition.

The pH of the ready-to-use composition may range from 4 to 12, such as, for example, from 7 to 11.5.

The pH of the composition may be adjusted using an acidifying or alkalifying agent chosen from those mentioned previously.

The present disclosure further relates to a method of coloring keratin fibers that comprises the application of a dyeing composition according to the present disclosure to wet or dry keratin fibers.

The application to the fibers of the dyeing composition comprising the compound(s) of formula (I), (II), and/or (III) or the acid addition salts thereof, optionally at least one oxidation base optionally combined with at least one coupler, and optionally at least one additional direct dye, may be performed in the presence of an oxidizing agent.

This oxidizing agent may be added to the composition comprising the compound(s) of formula (I), (II), and/or (III) and the optional oxidation bases, couplers and/or additional direct dyes, either at the time of use or directly on the keratin fiber.

The oxidizing composition may also include various adjuvants conventionally used in compositions for dyeing the hair and as defined above.

The pH of the oxidizing composition containing the oxidizing agent may be such that, after mixing with the dye composition, the pH of the resulting composition applied to the keratin fibers ranges from 4 to 12, such as, for example, from 7 to 11.5. The pH may be adjusted to the desired value by means of acidifying or alkalifying agents usually used in the dyeing of keratin fibers and as described above.

The composition that is finally applied to the keratin fibers may be in various forms, such as in the form of liquids, creams or gels or in any other form that is suitable for dyeing keratin fibers, such as human hair.

According to one embodiment, the composition according to the present disclosure is free of oxidation base and coupler.

The composition applied may optionally comprise at least one oxidizing agent.

The composition is thus applied to the wet or dry keratin fibers and is then left for a leave-in time that is sufficient to give the desired coloration.

Whatever the version adopted (with or without oxidizing agent), the leave-in time may range from a few seconds to one hour, such as, for example, from 3 to 30 minutes.

The temperature at which the composition is left to act generally ranges from 15 to 220° C., such as from 15 to 80° C. or from 15 to 40° C.

After the leave-in time, the composition may be removed by rinsing with water, optionally followed by washing with a shampoo, and then optionally by drying.

Another aspect of the present disclosure relates to a device having a plurality of compartments, i.e., a multi-compartment device, or dyeing kit, in which a first compartment contains the dyeing composition of the invention and a second compartment contains the oxidizing composition. This device may be equipped with a means for delivering the desired mixture to the hair, such as the devices described in French Patent No. FR 2 586 913

Other than in the operating examples, or where otherwise indicated, all numbers expressing quantities of ingredients, reaction conditions, and so forth ised in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches. Also, where the term "between" is used, the ranges defined include the stated endpoints.

Notwithstanding the numerical ranges and parameters setting forth the broad scope of the invention as approximations, the numerical values set forth in the specific examples are reported as precisely as possible. Any numerical value, however, inherently contains certain errors necessarily resulting from the standard deviation found in its respective testing measurement.

The examples that follow serve to illustrate the disclosure without, however, being limiting in nature.

EXAMPLES

Synthesis of Compound 4

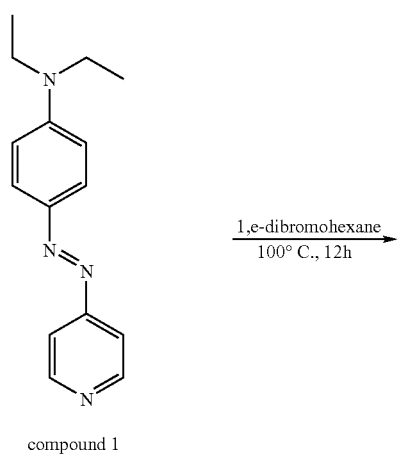

compound 1

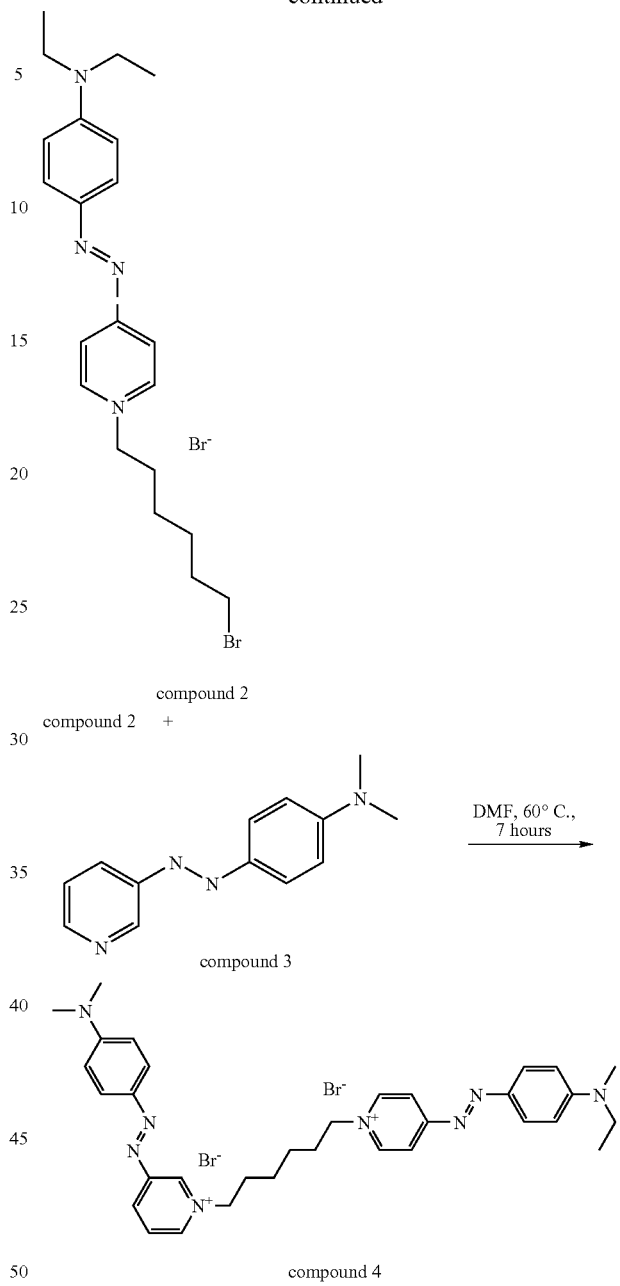

Compound 1 is available commercially (Interchim).

Compound 3 was obtained by coupling the diazonium salt of 3-aminopyridine to dimethylaniline.

Step 1:

Compound 1 (2.5 g) was reacted in the presence of 50 ml of 1,6-dibromohexane at 100° C. for 12 hours. The reaction mixture was brought to ambient temperature, water was added and then the product was extracted with dichloromethane. The product was dried over sodium sulphate, filtered and concentrated under vacuum to give a violet powder (2 g) corresponding to the structure of compound 2 above.

The $^1$H NMR and mass analyses were in accordance with the expected product.

Step 2:

Compound 2 (0.1 g) and 0.045 g of compound 3 were reacted in the presence of 1 ml of DMF at 60° C. for 7 days. The reaction mixture was brought to ambient temperature. A residue was obtained by precipitating the reaction mixture from diisopropyl ether. The residue was purified by liquid chromatography. A brown powder corresponding to the compound of compound 4 above was obtained.

The $^1$H NMR and mass analyses were in accordance with the expected product.

Compound 5 was obtained by coupling the diazonium salt of 3-aminopyridine to phenol.

Compound 2 (0.1 g) and 0.040 g of compound 5 were reacted in the presence of 1 ml of DMF at 60° C. for 7 days. The reaction mixture was brought to ambient temperature beforehand. A residue was obtained by precipitating the reaction mixture from diisopropyl ether. The residue was purified by liquid chromatography. A brown powder corresponding to the compound of structure 6 was obtained.

The $^1$H NMR and mass analyses were in accordance with the expected product.

Synthesis of Compound 6

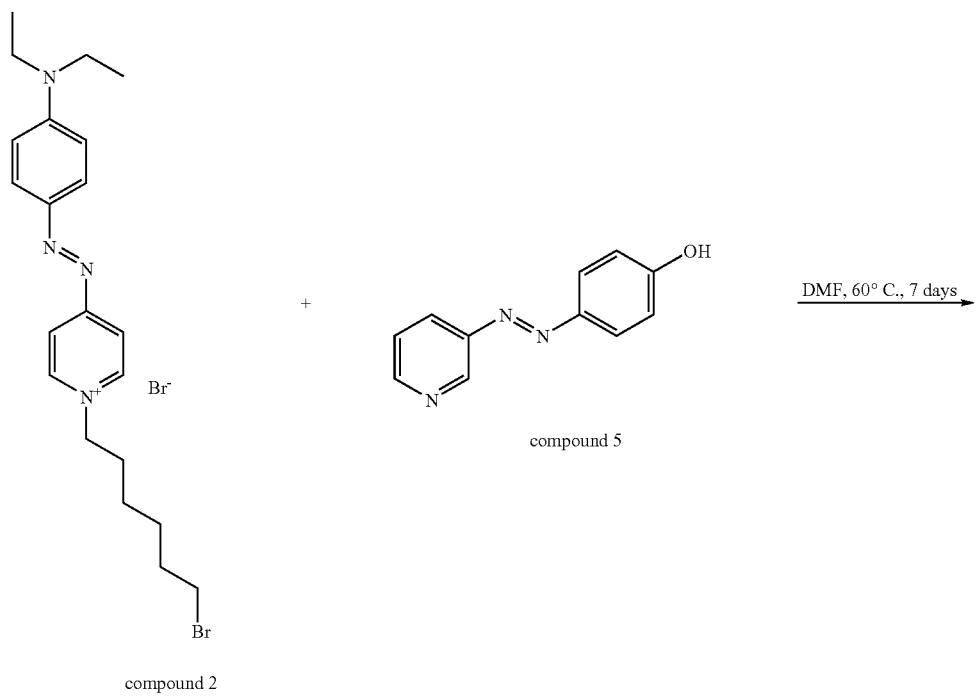

compound 2 compound 5

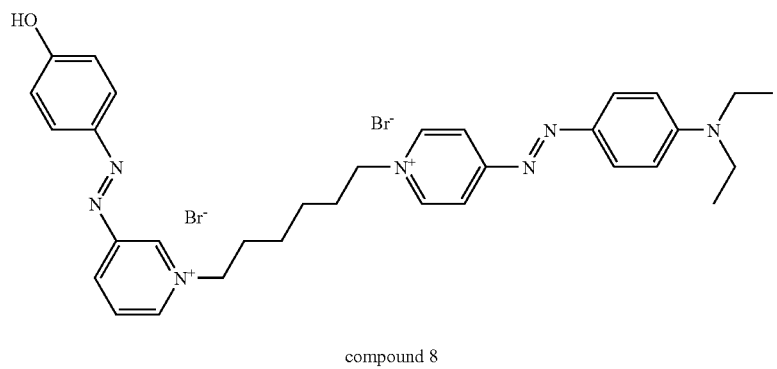

compound 8

Synthesis of Compound 10

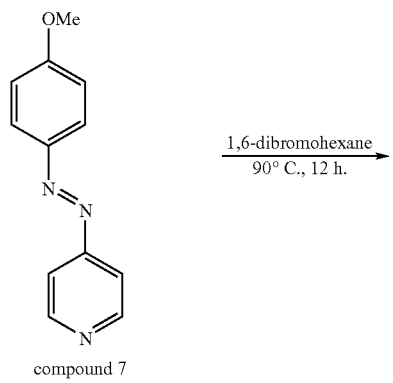

compound 7

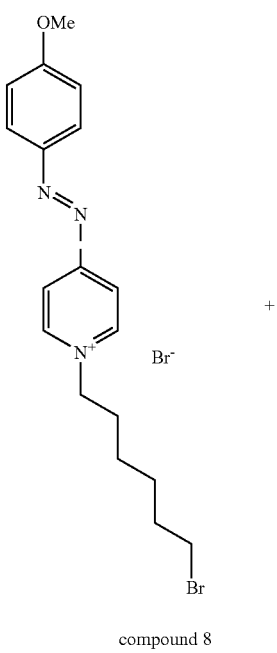

compound 8

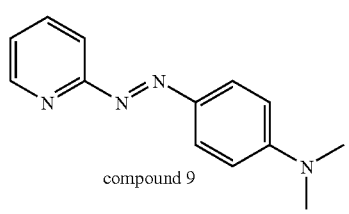

compound 9

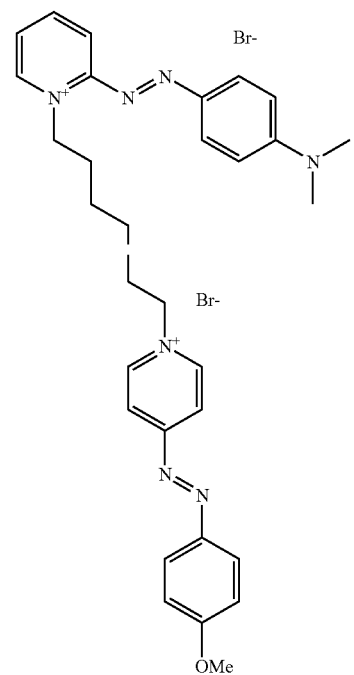

compound 10

Compound 7 was obtained in two steps:

Coupling reaction of the diazonium salt of 4-aminopyridine to phenol.

O-alkylation reaction in the presence of methanol and sulphuric acid.

Compound 9 is available commercially (Interchim).

Step 1:

Compound 7 (1.25 g) and 20 ml of 1,6-dibromohexane were reacted at 90° C. for 12 hours. The reaction mixture was brought to ambient temperature beforehand and then poured into a solution containing ethyl acetate. The resulting precipitate was isolated by filtration and then dried under vacuum. An orange-yellow powder corresponding to the compound of structure 8 was obtained.

The $^1$H NMR and mass analyses were in accordance with the expected product.

Step 2:

Compound 8 (1 g) and 0.49 g of compound 9 were reacted in the presence of 10 ml of DMF at 100° C. for 24 hours. The reaction mixture was brought to ambient temperature. A residue was obtained by precipitating the reaction mixture from diisopropyl ether. The residue was purified by liquid chromatography. A dark purple-red powder corresponding to the compound of structure 10 was obtained.

The $^1$H NMR and mass analyses were in accordance with the expected product.

Synthesis of Compound 11

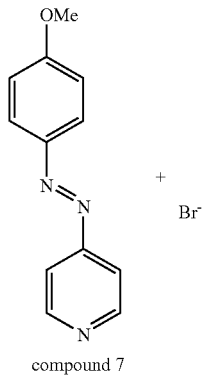

compound 7

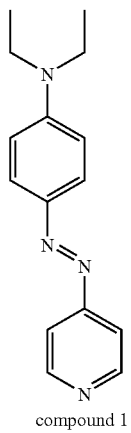

compound 1

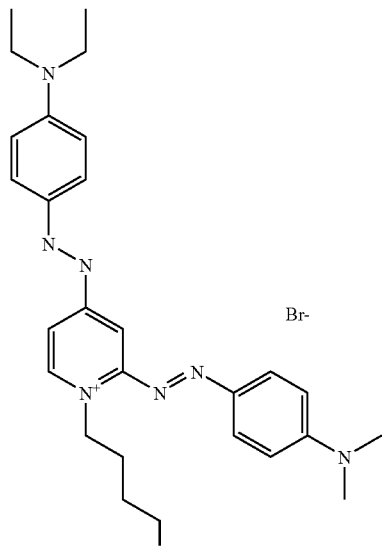

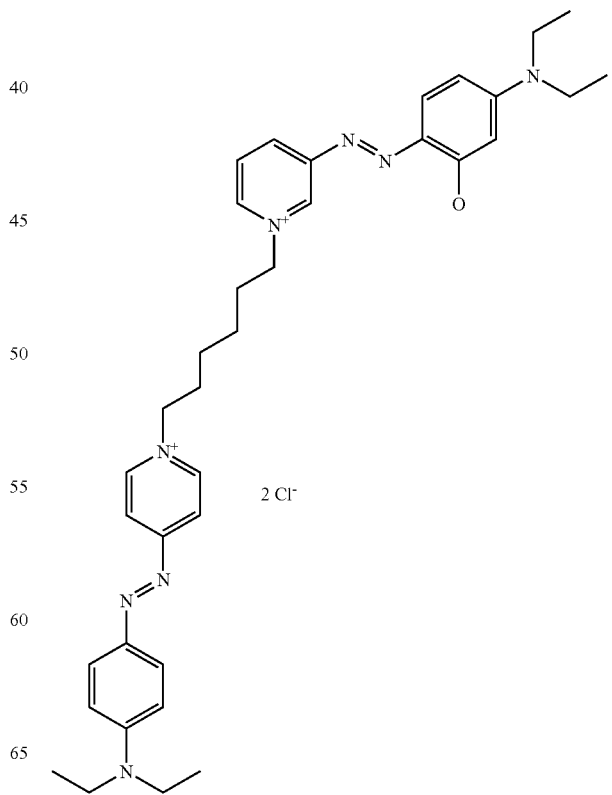

compound 11

Step 2:

Compound 8 (1 g) and 0.52 g of compound 1 were reacted in the presence of 10 ml of DMF at 100° C. for 24 hours. The reaction mixture was brought to ambient temperature. A residue was obtained by precipitating the reaction medium from diisopropyl ether. The residue was purified by liquid chromatography. A dark purple-red powder corresponding to the compound of structure 11 was obtained.

The $^1$H NMR and mass analyses were in accordance with the expected product.

Synthesis of Compound 15: Synthesis of 3-{(E)-[4-(diethylamino)-2-hydroxphenyl]diazenyl}-1-[6-(4-{(E)-[4-(diethylamino)phenyl]diazenyl}pyridinium-1-yl)hexyl]pyridinium dichloride Compound 15

Step 1: Synthesis of 5-(diethylamino)-2-[(E)-pyridin-3-yl-diazenyl]phenol

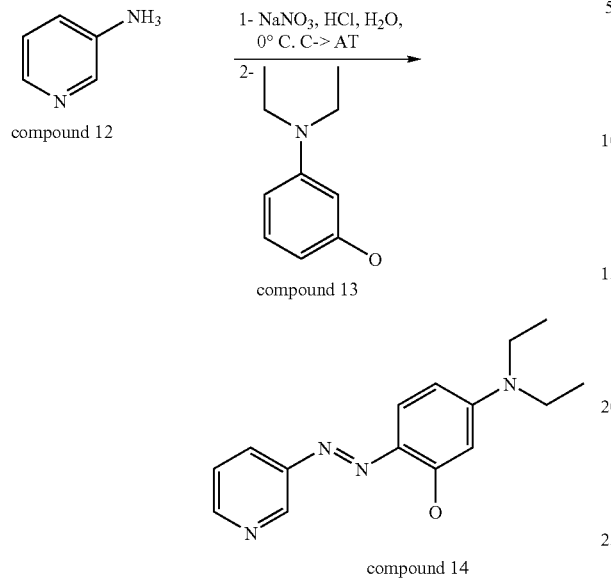

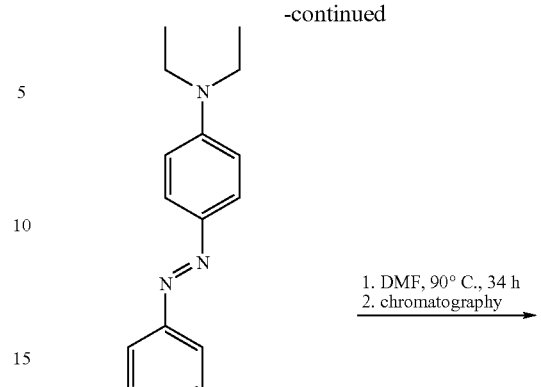

Compound 13 is available commercially.

In a three-necked flask with a top-mounted condenser, compound 12 (1.32 g) was dissolved at 0° C. in the presence of 10 ml of water. 7.5 ml of 5N hydrochloric acid solution was added to the preceding reaction mixture.

0.97 g of sodium nitrite was dissolved in 6 ml of water. This solution was cooled beforehand and then added slowly to the reaction mixture at 0° C. with stirring to give a diazonium salt solution.

2.13 g of compound 13 was dissolved in 4 ml of methanol. This solution was cooled beforehand, and the diazonium salt obtained previously was added slowly at 0° C. with stirring. The reaction mixture then took on a darkened coloration.

The pH of the reaction mixture was subsequently brought to 8 using 1M sodium hydroxide solution. The resulting precipitate was isolated by filtration and washed a number of times with diethyl ether and then dried under vacuum. 3.2 g of an orange-colored powder corresponding to compound 14 was obtained. The analyses were in accordance with the expected product.

Step 2: Synthesis of 3-{(E)-[4-(diethylamino)-2-hydroxyphenyl]diazenyl}-1-[6-(4-{(E)-[4-(diethylamino)phenyl]diazenyl}pyridinium-1-yl)hexyl]pyridinium dichloride

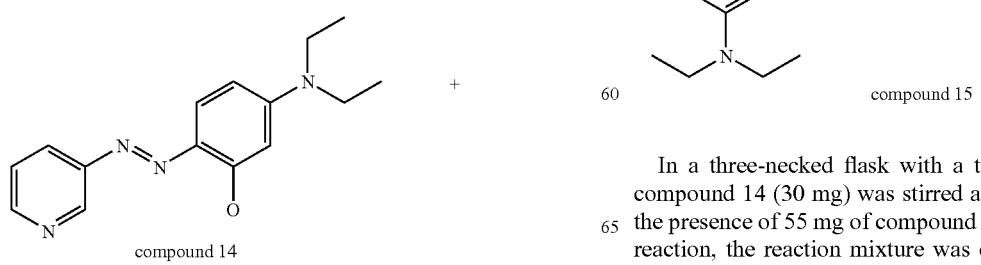

In a three-necked flask with a top-mounted condenser, compound 14 (30 mg) was stirred at 90° C. for 34 hours in the presence of 55 mg of compound 2 in 8 ml of DMF. After reaction, the reaction mixture was cooled to ambient temperature and then poured into diethyl ether (50 ml). The resulting precipitate was isolated by filtration and washed a number of times with diethyl ether and then ethyl acetate. The washed precipipate was then dried under vacuum. The residue obtained was purified by semi-preparative HPLC. Counterion exchange was performed in the course of this purification. 6.1 mg of a dark brown powder corresponding to compound 15 was obtained.

The analyses were in accordance with the expected product.

Dyeing Examples

The following dyeing compositions were prepared:

| Dye | $10^{-3}$ mol |
|---|---|
| Dyeing vehicle | (*) |
| Demineralized water qs | 100 g |

(*): dyeing vehicle (1) pH 7 or (2) pH 9.5

| Dyeing vehicle (1) pH 7: | |
|---|---|
| 96° ethyl alcohol | 20.8 g |
| Pentasodium salt of diethylenetriamine-pentaacetic acid in aqueous solution at 40% | 0.48 g as** |
| C8–C10 alkyl polyglucoside in aqueous solution at 60% | 3.6 g as |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

| Dyeing vehicle (2) pH 9.5: | |
|---|---|
| 96° ethyl alcohol | 20.8 g |
| Pentasodium salt of diethylenetriamine-pentaacetic acid in aqueous solution at 40% | 0.48 g as** |
| C8–C10 alkyl polyglucoside in aqueous solution at 60% | 3.6 g as |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

**as = active substance

For colorations under non-lightening conditions (without oxidizing agent), these compositions were applied directly to the hair.

For the colorations under lightening conditions, an oxidizing medium was used. In this case, at the time of use, each composition was mixed with an equal weight of 20-volume hydrogen peroxide (6% by weight). A final pH of 7 or 9.5 was obtained.

Each resulting mixture was applied to grey tresses containing 90% white hair, with a 6:1 bath ratio. After being left in for 30 minutes, the tresses were rinsed, washed with a standard shampoo, rinsed again and then dried.

The dyeing results obtained were as follows:

| | pH 7 (without oxidizing agent) | pH 9.5 (without oxidizing agent) | pH 7 (with oxidizing agent) | pH 9.5 (with oxidizing agent) |
|---|---|---|---|---|
| Compound 4 | intense violet | intense violet | intense violet | intense violet |

The tresses thus colored were subjected to a wash resistance test, which consists of 12 shampooings (with a standard shampoo) followed by evaluation of the color. After 12 shampooings the tresses were still colored.

What is claimed is:

1. A dissymmetrical cationic diazo compound chosen from those of formula (I), (II) and (III) below, their resonance forms, acid addition salts, and solvates, and mixtures thereof, wherein in the compounds of formulae (I), (II), and (III), the formula members attached to each side of the linker L are either compositionally different or positionally different such that the compounds as a whole are dissymmetrical:

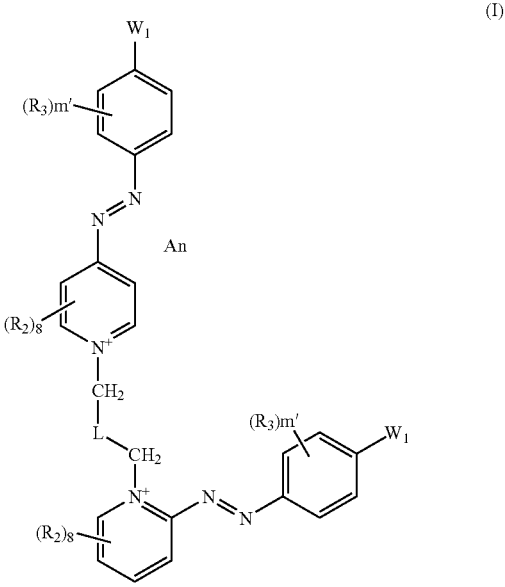

(I)

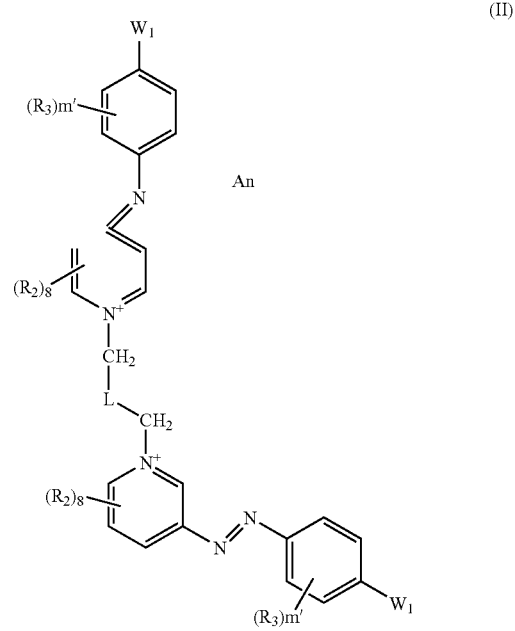

(II)

-continued

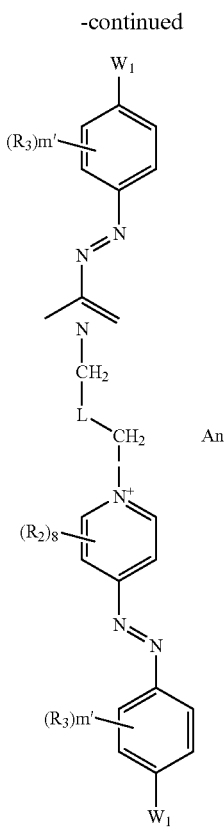

(III)

wherein:
the radicals $R_2$, which are identical or different, independently of one another are chosen from:
$C_1$-$C_{16}$ alkyl radicals optionally interrupted by at least one heteroatom and/or at least one group containing at least one heteroatom, said alkyl radicals being optionally substituted by at least one group chosen from hydroxyl, $C_1$-$C_2$ alkoxy, $C_2$-$C_4$ (poly)hydroxyalkoxy, amino, $C_1$-$C_2$ (di)alkylamino, thio (—SH), $C_1$-$C_4$ thioalkyl, $C_1$-$C_4$ alkylsulphinyl, and $C_1$-$C_4$ alkylsulphonyl groups;
hydroxyl groups;
$C_1$-$C_4$ alkoxy groups;
$C_2$-$C_4$ (poly)hydroxyalkoxy groups;
$C_2$-$C_4$ (poly)hydroxyalkylamino groups;
alkoxycarbonyl groups (RO—CO—) wherein R is a $C_1$-$C_4$ alkyl radical;
alkylcarbonyloxy groups (RCO—O—) wherein R is a $C_1$-$C_4$ alkyl radical;
alkylcarbonyl groups (R—CO—) wherein R is a $C_1$-$C_4$ alkyl radical;
amino groups;
amino groups substituted by one or two identical or different $C_1$-$C_4$ alkyl radicals optionally carrying at least one hydroxyl group, wherein the two alkyl radicals may optionally form, with the nitrogen atom to which they are attached, a heterocycle containing 1 to 3 heteroatoms chosen from N, O and S, and containing 5 to 7 ring members, wherein said heterocycle is saturated or unsaturated, aromatic or non-aromatic and is optionally substituted;
alkylcarbonylamino groups (RCO—NR'—) wherein R is a $C_1$-$C_4$ alkyl radical and R' is chosen from hydrogen and a $C_1$-$C_4$ alkyl radical;
aminocarbonyl groups ((R)$_2$N—CO—) wherein radicals R independently of one another are chosen from a hydrogen atom and a $C_1$-$C_4$ alkyl radical;
ureido groups (N(R)$_2$—CO—NR'—) wherein radicals R and R' independently of one another are chosen from a hydrogen atom and a $C_1$-$C_4$ alkyl radical;
aminosulphonyl groups ((R)$_2$N—SO$_2$—) wherein radicals R independently of one another are chosen from a hydrogen atom and a $C_1$-$C_4$ alkyl radical;
alkylsulphonylamino groups (RSO$_2$—NR'—) wherein R is a $C_1$-$C_4$ alkyl radical and R' is chosen from a hydrogen atom and a $C_1$-$C_4$ alkyl radical;
optionally substituted aryl radicals;
optionally substituted ($C_1$-$C_4$)alkylaryl radicals;
alkylsulphinyl groups (R—SO—) wherein R is a $C_1$-$C_4$ alkyl radical;
alkylsulphonyl groups (R—SO$_2$—) wherein R is a $C_1$-$C_4$ alkyl radical;
nitro groups;
cyano groups;
halogen atoms;
thio groups (HS—);
alkylthio groups (RS—) wherein R is an optionally substituted $C_1$-$C_4$ alkyl radical; and
when e is 2, for each of the formulae (I), (II), and (III), two radicals $R_2$ may optionally form, with the carbon atoms to which they are attached, a secondary ring, aromatic or non-aromatic, containing 5 or 6 ring members, which is optionally substituted by at least one identical or different group chosen from hydroxyl, $C_1$-$C_4$ alkyl, $C_1$-$C_4$ alkoxy, $C_2$-$C_4$ (poly)hydroxyalkoxy, amino, and amino substituted by one or two identical or different $C_1$-$C_4$ alkyl radicals which optionally carry at least one group chosen from hydroxyl and methylcarbonylamino groups;
e is an integer ranging from 0 to 4; when e is less than 4, the unsubstituted carbon atom(s) of the heterocycle of the formulae (I), (II), and (III) carry a hydrogen atom;
the radicals $R_3$, from formulae (I), (II), and (III), which are identical or different, independently of one another are chosen from:
optionally substituted $C_1$-$C_{16}$ alkyl radicals optionally interrupted by at least one heteroatom or by at least one group containing at least one heteroatom;
hydroxyl groups;
$C_1$-$C_4$ alkoxy groups;
$C_2$-$C_4$ (mono) or (poly)hydroxyalkoxy groups;
alkoxycarbonyl groups (RO—CO—) wherein R is a $C_1$-$C_4$ alkyl radical;
alkylcarbonyloxy groups (RCO—O—) wherein R is a $C_1$-$C_4$ alkyl radical;
alkylcarbonyl groups (R—CO—) wherein R is a $C_1$-$C_4$ alkyl radical;
amino groups;
amino groups substituted by one or two identical or different $C_1$-$C_4$ alkyl radicals optionally carrying at least one group chosen from hydroxyl and $C_1$-$C_4$ alkoxy groups; wherein the two alkyl radicals may optionally form, with the nitrogen atom to which they are attached, a heterocycle containing 1 to 3 heteroatoms chosen from N, O and S, containing 5 to 7 ring members, and which is saturated or unsaturated, aromatic or non-aromatic and is optionally substituted;

alkylcarbonylamino groups (RCO—NR'—) wherein the radical R is a $C_1$-$C_4$ alkyl radical and the radical R' is chosen from a hydrogen atom and a $C_1$-$C_4$ alkyl radical;

aminocarbonyl groups ((R)$_2$N—CO—) wherein radicals R independently of one another are chosen from a hydrogen atom and a $C_1$-$C_4$ alkyl radical;

ureido groups (N(R)$_2$—CO—NR'—) wherein radicals R and R' independently of one another are chosen from a hydrogen atom and a $C_1$-$C_4$ alkyl radical;

aminosulphonyl groups ((R)$_2$N—SO$_2$—) wherein radicals R independently of one another are chosen from a hydrogen atom and a $C_1$-$C_4$ alkyl radical;

alkylsulphonylamino groups (RSO$_2$—NR'—) wherein radicals R and R' independently of one another are chosen from a hydrogen atom and a $C_1$-$C_4$ alkyl radical;

thio groups (HS—);

alkylthio groups (RS—) wherein R is a $C_1$-$C_4$ alkyl radical;

alkylsulphinyl groups (R—SO—) wherein R is a $C_1$-$C_4$ alkyl radical;

alkylsulphonyl groups (R—SO$_2$—) wherein R is a $C_1$-$C_4$ alkyl radical;

nitro groups;

cyano groups;

halogen atoms; and when m' is greater than or equal to 2, two adjacent radicals R$_3$ may form, with the carbon atoms to which they are attached, a secondary ring, aromatic or non-aromatic containing 6 ring members, which is optionally substituted by at least one identical or different group chosen from: hydroxyl, —NR$_4$—Ph, —NR$_4$—Ph—NR$_5$R$_6$, —NR$_4$—Ph—OR$_7$, $C_1$-$C_4$ alkyl, $C_1$-$C_4$ alkoxy, $C_2$-$C_4$ (poly)hydroxyalkoxy, $C_1$-$C_4$ alkylcarbonylamino, amino, and amino substituted by one or two identical or different $C_1$-$C_4$ alkyl radicals which optionally carry at least one hydroxyl group;

m' is an integer from 0 to 4; when m' is less than 4, then the unsubstituted carbon atom(s) of the aromatic ring of the formulae (I), (II), and (III) carry a hydrogen atom;

the W$_1$ groups of the formulae (I), (II), and (III), which are identical or different, independently of one another, are chosen from:

hydrogen atoms;

halogen atoms chosen from bromine, chlorine and fluorine; and a group chosen from —NR$_5$R$_6$, OR$_7$, —NR$_4$—Ph—NR$_5$R$_6$, —NR$_4$—Ph—OR$_7$, —O—Ph—OR$_7$ and —O—Ph—NR$_5$R$_6$ groups, wherein:

R$_4$ and R$_7$, which may be identical or different, are independently chosen from a hydrogen atom, an optionally substituted $C_1$-$C_{20}$ alkyl radical, an optionally substituted aryl or aralkyl radical and an optionally substituted phenyl radical;

R$_5$ and R$_6$, which are identical or different, are chosen from a hydrogen atom, an optionally substituted $C_1$-$C_{20}$ alkyl radical, an optionally substituted phenyl radical, an optionally substituted aryl or aralkyl radical and an alkylcarbonyl radical (R—CO—) wherein R is a $C_1$-$C_4$ alkyl radical; and R$_5$ and R$_6$ may optionally form, with the nitrogen atom to which they are attached, a heterocycle containing 1 to 3 heteroatoms, chosen from N, O and S, and containing 5 to 7 ring members, which is saturated or unsaturated, aromatic or non-aromatic and is optionally substituted; or R$_5$ and R$_6$ may optionally form, with the carbon atom of the aromatic ring that is optionally substituted by a hydroxyl and adjacent to that to which —NR$_5$R$_6$ is attached, a 5- or 6-membered saturated or unsaturated heterocycle;

Ph is an optionally substituted phenyl radical;

L is chosen from a cationic linker and a non-cationic linker; and

An is chosen from at least one identical or different cosmetically acceptable anions which ensure the electroneutrality of the compounds of formulas (I), (II) and (III).

2. The compound according to claim 1, wherein when R$_2$ and/or R$_3$ is chosen from optionally substituted $C_1$-$C_{16}$ alkyl radicals optionally interrupted by at least one heteroatom and/or at least one group containing at least one heteroatom, said heteroatoms and said groups are chosen from oxygen, nitrogen, sulphur, —CO—, SO$_2$—, and combinations thereof.

3. The compound according to claim 1, wherein said radicals R$_2$, which are identical or different, are chosen from:

a halogen atom chosen from chlorine and fluorine;

$C_1$-$C_4$ alkyl radicals optionally substituted by at least one identical or different radical chosen from hydroxyl, $C_1$-$C_2$ alkoxy, $C_2$-$C_4$ (poly)hydroxyalkoxy, amino, $C_1$-$C_2$ (di)alkylamino, thio (—SH), $C_1$-$C_4$ alkylsulphinyl, $C_1$-$C_4$ alkylsulphonyl and $C_1$-$C_4$ thioalkyl radicals;

phenyl radicals optionally substituted by at least one identical or different radical chosen from hydroxyl, $C_1$-$C_2$ alkoxy, $C_2$-$C_4$ (poly)hydroxyalkoxy, amino and $C_1$-$C_2$ (di)alkylamino radicals and a halogen atom;

$C_1$-$C_4$ alkoxy radicals;

$C_1$-$C_4$ alkylsulphonylamino radicals;

$C_2$-$C_4$ (poly)hydroxyalkoxy radicals;

an amino radical;

$C_1$-$C_2$ (di)alkylamino radicals;

$C_2$-$C_4$ (poly)hydroxyalkylamino radicals;

alkylsulphonylamino radicals (RSO$_2$—NR'—) wherein R is a $C_1$-$C_4$ alkyl radical and R' is chosen from a hydrogen atom and a $C_1$-$C_4$ alkyl radical;

aminosulphonyl radicals ((R)$_2$NSO$_2$—) wherein said radicals R independently of one another are chosen from a hydrogen atom and a $C_1$-$C_4$ alkyl radical;

alkylthio radicals (RS—) wherein said radical R is a $C_1$-$C_4$ alkyl radical;

alkylsulphinyl radicals (RSO—) wherein said radical R is a $C_1$-$C_4$ alkyl radical;

alkylsulphonyl radicals (R—SO$_2$—) wherein said radical R is a $C_1$-$C_4$ alkyl radical; and alkylcarbonylamino radicals (RCONR'—) wherein said radical R is chosen from a hydrogen atom and a $C_1$-$C_4$ alkyl radical and radical R' is chosen from a hydrogen atom and a $C_1$-$C_4$ alkyl radical.

4. The compound according to claim 1, wherein when e is 2 the two radicals R$_2$ from formulae (I), (II), and (III) may optionally form, together with the carbon atoms to which they are attached, a secondary, 6-membered aromatic ring that is optionally substituted with at least one identical or different group chosen from hydroxyl, $C_1$-$C_4$ alkyl, $C_1$-$C_4$ alkoxy, amino, and amino substituted by one or two identical or different $C_1$-$C_4$ alkyl groups that optionally carry at least one hydroxyl or methylcarbonylamino group.

5. The compound according to claim 1, wherein the radicals $R_3$, which may be identical or different, are chosen from:
optionally substituted $C_1$-$C_{16}$ alkyl radicals;
a halogen atom;
a hydroxyl group;
$C_1$-$C_2$ alkoxy radicals;
a $C_2$-$C_4$ (poly)hydroxyalkoxy radical;
an amino radical;
amino radicals substituted by one or two identical or different $C_1$-$C_4$ alkyl radicals which optionally carry at least one identical or different group chosen from hydroxyl and $C_1$-$C_4$ alkoxy, wherein the two alkyl radicals may optionally form, with the nitrogen atom to which they are attached, a heterocycle containing 1 to 3 heteroatoms chosen from N, O and S, the heterocycle containing 5 to 7 ring members, being saturated or unsaturated, aromatic or non-aromatic, and being optionally substituted;
alkylcarbonylamino radicals (RCO—NR'—) wherein the radical R is a $C_1$-$C_4$ alkyl radical and the radical R' is chosen from a hydrogen and a $C_1$-$C_4$ alkyl radical;
alkylsulphonylamino radicals (R'SO$_2$—NR—) wherein the radical R is chosen from a hydrogen atom and a $C_1$-$C_4$ alkyl radical and the radical R' is a $C_1$-$C_4$ alkyl radical;
aminosulphonyl radicals ((R)$_2$N—SO$_2$—) wherein the radicals R, which are identical or different, are chosen from a hydrogen atom and a $C_1$-$C_4$ alkyl radical;
alkylthio radicals (RS—) wherein the radical R is a $C_1$-$C_4$ alkyl radical; and
alkylsulphonyl radicals (R—SO$_2$—) wherein the radical R is a $C_1$-$C_4$ alkyl radical.

6. The compound according to claim 1, wherein the radicals $R_3$, which may be identical or different, are chosen from:
$C_1$-$C_4$ alkyl radicals which are optionally substituted by at least one identical or different radical chosen from hydroxyl radicals, $C_1$-$C_2$ alkylcarbonylamino radicals, amino radicals substituted by two identical or different $C_1$-$C_2$ alkyl radicals which optionally carry at least one identical or different group chosen from hydroxyl or $C_1$-$C_2$ alkoxy, wherein the two alkyl radicals may optionally form, with the nitrogen atom to which they are attached, a 5- or 6-membered heterocycle which is saturated or unsaturated and is optionally aromatic;
$C_2$-$C_4$ hydroxyalkoxy radicals;
a halogen chosen from chlorine and fluorine;
an amino radical;
amino radicals substituted by one or two identical or different $C_1$-$C_2$ alkyl radicals which optionally carry at least one hydroxyl group;
a methylcarbonylamino radical;
a methylsulphonylamino radical;
a hydroxyl radical;
$C_1$-$C_2$ alkoxy radicals; and
a methylsulphonyl radical.

7. The compound according to claim 6, wherein when $R_3$ is chosen from $C_1$-$C_4$ alkyl radicals substituted by amino radicals substituted by two identical or different $C_1$-$C_2$ alkyl radicals and wherein when the two alkyl radicals optionally form, with the nitrogen atom to which they are attached, a 5- or 6-membered saturated or unsaturated and optionally aromatic heterocycle, said heterocycle is chosen from pyrrolidine, piperazine, homopiperazine, pyrrole, imidazole and pyrazole.

8. The compound according to claim 1, wherein when the coefficient m' is greater than or equal to 2, two adjacent radicals $R_3$ may form, with the carbon atoms to which they are attached, a secondary, 6-membered aromatic ring optionally substituted by at least one identical or different group chosen from hydroxyl groups, —NR$_4$—Ph, —NR$_4$—Ph—NR$_5$R$_6$ and —NR$_4$—Ph—OR$_7$ groups, $C_1$-$C_4$ alkyl groups, $C_1$-$C_4$ alkoxy groups, $C_2$-$C_4$ (mono) or (poly)hydroxyalkoxy groups, $C_1$-$C_4$ alkylcarbonylamino groups, amino groups, and amino groups substituted by one or two identical or different $C_1$-$C_4$ alkyl radicals which optionally carry at least one hydroxyl group.

9. The compound according to claim 8, wherein two adjacent radicals $R_3$ may form, with the carbon atoms to which they are attached, a secondary, 6-membered aromatic ring which is optionally substituted by at least one identical or different group chosen from hydroxyl, methoxy, ethoxy, 2-hydroxyethyloxy, amino, methylcarbonylamino, (di)-2-hydroxyethylamino, —NH—Ph, —NH—Ph—NH$_2$, —NH—Ph—NHCOCH$_3$, —NH—Ph—OH and —NH—Ph—OCH$_3$ groups.

10. The compound according to claim 1, wherein $R_4$ and $R_7$ independently of one another are chosen from:
a hydrogen atom;
$C_1$-$C_6$ alkyl radicals which are optionally substituted by at least one identical or different group; and
an aryl or arylalkyl radical, the aryl moiety being optionally substituted by at least one identical or different group.

11. The compound according to claim 10, wherein when $R_4$ and $R_7$ independently of one another are chosen from an aryl or arylalkyl radical, the aryl moiety is optionally substituted by at least one identical or different group chosen from a chlorine atom, an amino group, a hydroxyl group, $C_1$-$C_2$ alkoxy groups and amino groups which are mono- or disubstituted by two identical or different $C_1$-$C_4$ alkyl radicals which optionally carry at least one hydroxyl group.

12. The compound according to claim 10, wherein when $R_4$ and $R_7$ independently of one another are chosen from $C_1$-$C_6$ alkyl radicals, the alkyl radicals may be optionally substituted by at least one identical or different group chosen from hydroxyl and $C_1$-$C_2$ alkoxy.

13. The compound according to claim 1, wherein the radicals $R_5$ and $R_6$, which are identical or different, are chosen from:
a hydrogen atom;
alkylcarbonyl radicals (R—CO—) wherein R is an optionally substituted $C_1$-$C_4$ alkyl radical;
a $C_1$-$C_6$ alkyl radical which is optionally substituted by at least one identical or non-identical group chosen from hydroxyl, $C_1$-$C_2$ alkoxy, amino, $C_1$-$C_4$ (di)alkylamino; the alkyl radical may further be substituted by at least one identical or different group chosen from $C_1$-$C_4$ alkylsulphonyl, $C_1$-$C_4$ alkylsulphinyl and $C_1$-$C_4$ alkylcarbonyl; and
an aryl or arylalkyl radical, the awl moiety being optionally substituted by at least one identical or different radical.

14. The compound according to claim 13, wherein when the radicals $R_5$ and $R_6$, which are identical or different are chosen from an aryl or arylalkyl radical, the awl moiety may be optionally substituted by at least one identical or different radical chosen from a chlorine atom, an amino group, a hydroxyl group, a $C_1$-$C_4$ alkoxy group and an amino group which is mono- or disubstituted by two identical or different $C_1$-$C_4$ alkyl radicals which optionally carry at least one hydroxyl group.

15. The compound according to claim 1, wherein the radicals $R_5$ and $R_6$, which are identical or different, are chosen from:
  a hydrogen atom;
  methylcarbonyl, ethylcarbonyl and propylcarbonyl radicals;
  optionally substituted $C_1$-$C_3$ alkyl radicals; and
  a phenyl radical which is optionally substituted by at least one identical or different radical chosen from hydroxyl radicals, $C_1$-$C_2$ alkoxy radicals, amino radicals, amino radicals substituted by at least one identical or different $C_1$-$C_4$ alkyl group which optionally carries at least one hydroxyl group.

16. The compound according to claim 15, wherein when the radicals $R_5$, and $R_6$, which are identical or different, are chosen from optionally substituted $C_1$-$C_3$ alkyl radicals, said radicals are chosen from methyl, ethyl, 2-hydroxyethyl and 2-methoxyethyl radicals.

17. The compound according to claim 1, wherein the heterocycle comprising from 5 to 7 ring members is chosen from the following heterocycles: piperidine, 2-(2-hydroxyethylpiperidine), 4-(aminomethyl)piperidine, 4-(2-hydroxyethyl)-piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine, 1-methyl-1,4-perhydrodiazepine, pyrrole, 1,4-dimethylpyrrole, 1-methyl-4-ethylpyrrole, and 1-methyl-4-propylpyrrole.

18. The compound according to claim 1, wherein $R_5$ and $R_6$ may form, together with the carbon atom of the aromatic ring that is optionally substituted by a hydroxyl and adjacent to that to which —$NR_5R_6$ is attached, a 5- or 6-membered unsaturated heterocycle.

19. The compound according to claim 1, wherein L is a non-cationic linker chosen from:
  a covalent bond;
  an optionally substituted $C_1$-$C_{40}$ alkyl radical optionally interrupted by a saturated or unsaturated, aromatic or non-aromatic heterocycle comprising from 3 to 7 ring members, wherein said heterocycle may be optionally substituted and optionally fused; said alkyl radical being optionally interrupted by at least one heteroatom and/or by at least one group comprising at least one heteroatom, wherein the linker L does not comprise an azo, nitro, nitroso or peroxo bond; and
  an optionally substituted phenyl radical.

20. The compound according to claim 19, wherein when L is chosen from an optionally substituted $C_1$-$C_{40}$ alkyl radical optionally interrupted by at least one heteroatom or by at least one group containing at least one heteroatom, said heteroatoms and groups are chosen from oxygen, nitrogen, sulphur, —CO—, $SO_2$—, and combinations thereof.

21. The compound according to claim 1, wherein L is a cationic linker chosen from a $C_2$-$C_{40}$ alkyl radical that carries at least one cationic charge and is optionally substituted and for interrupted by at least one saturated or unsaturated, aromatic or non-aromatic, identical or different heterocycle comprising from 3 to 7 ring members and/or optionally interrupted by at least one heteroatom and/or by at least one group comprising at least one heteroatom; wherein the linker L does not comprise an azo, nitro, nitroso or peroxo bond and the linker L carries at least one cationic charge.

22. The compound according to claim 21, wherein said heteroatoms and groups are chosen from oxygen, nitrogen, sulphur, —CO—, $SO_2$—, and combinations thereof.

23. The compound according to claim 1, wherein An is chosen from an organic anion, inorganic anion, and an anion mixture allowing the charge or charges on the compounds of formula (I), (II) and (III) to be balanced and wherein An is chosen from halides, hydroxides, sulphates, hydrogensulphates, alkylsulphates wherein the alkyl moiety is linear or branched and is $C_1$-$C_6$, carbonates, hydrogen carbonates, carboxylic acid salts, alkylsulphonates wherein the alkyl moiety is linear or branched and is $C_1$-$C_6$ alkyl; arylsulphonates wherein the aryl moiety is optionally substituted with at least one $C_1$-$C_4$ alkyl, and alkylsulphonyls.

24. The compound according to claim 23, wherein in the definition of An,
  the halides are chosen from chloride, bromide, fluoride, and iodide,
  the alkylsulphates wherein the linear or branched alkyl moiety is $C_1$-$C_6$ are chosen from a methylsulphate ion and an ethylsulphate ion;
  the salts of carboxylic acids are chosen from formate, acetate, citrate, tartrate, and oxalate;
  the alkylsulphonates wherein the linear or branched alkyl moiety is $C_1$-$C_6$ are methylsulphonate ions;
  the aryl moiety of the arylsulphonates is phenyl and is optionally substituted by at least one $C_1$-$C_4$ alkyl radical chosen from 4-tolylsulphonate; and/or
  the alkylsulphonyls are chosen from mesylate.

25. The compound according to claim 1, wherein said compound is chosen from those of formula (I'), (I'') (I'''), (II'), (II''), (II'''), (III'), (III''), and (III''') below, and resonance forms, acid addition salts, solvates, and mixtures thereof;

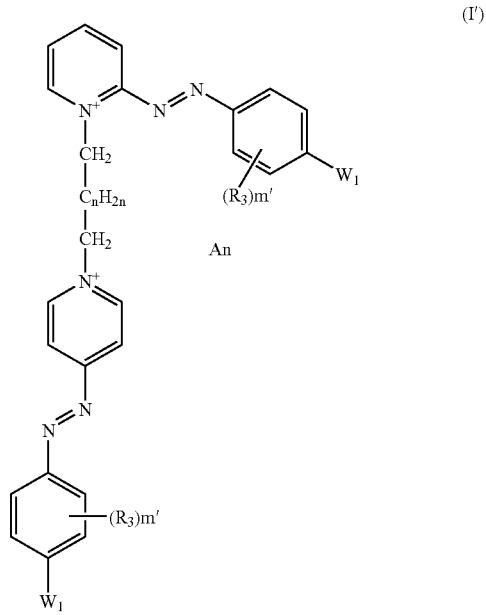

(I')

-continued
(I″)
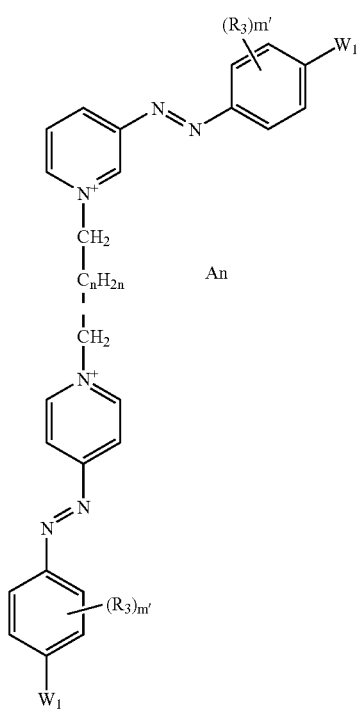
(I‴)
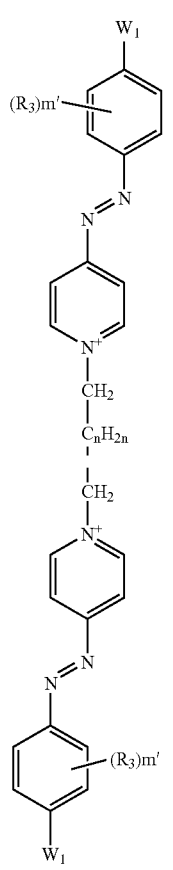
-continued
(II′)
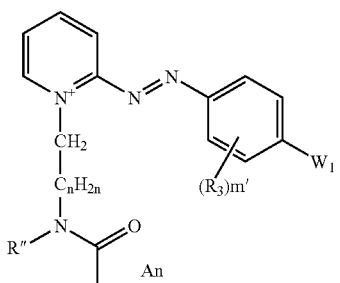
An
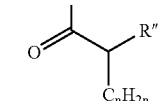
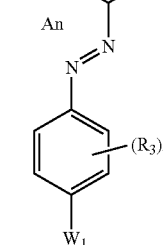
R″ = H, Me
n = integer between 1 and 6
(II″)
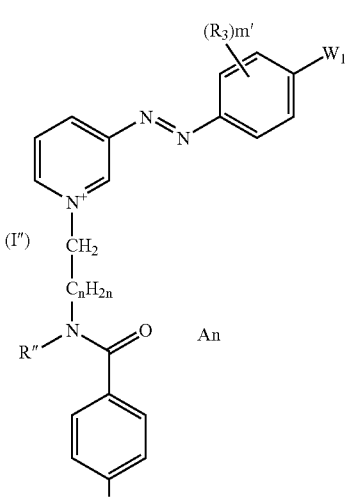

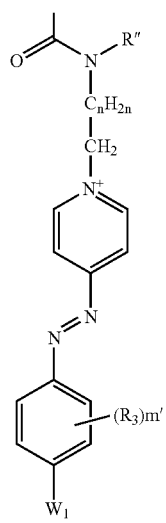
R″ = H, Me
n = integer between 1 and 6
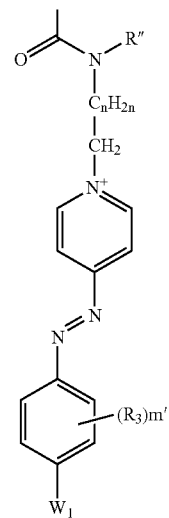
R″ = H, Me
n = integer between 1 and 6
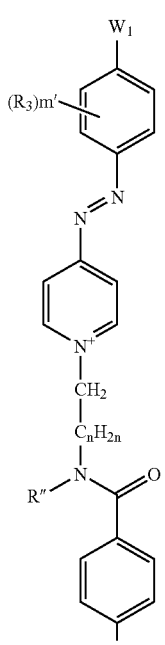
(II‴)
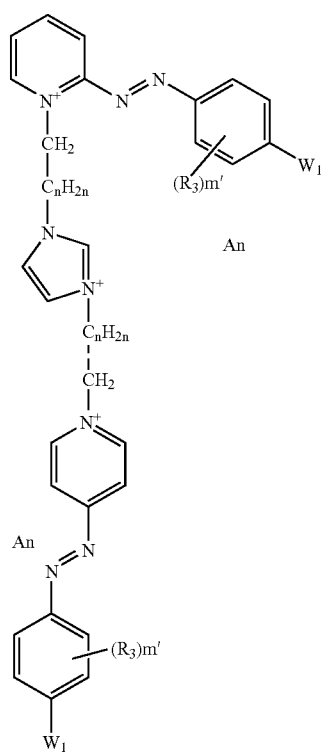
(III′)
n = integer between 2 and 5

-continued

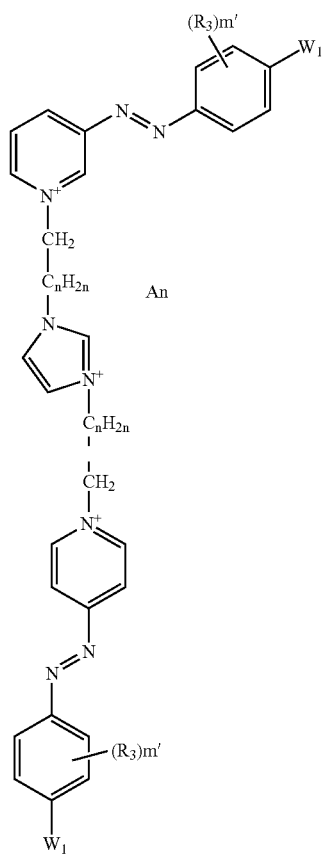

n = integer between 2 and 5

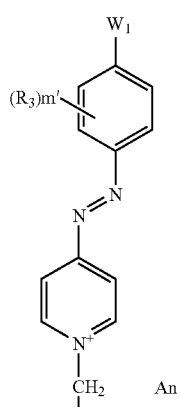

(III')

(III'') 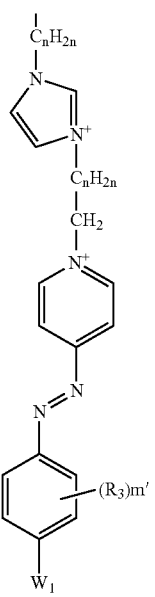

n = integer between 2 and 5 wherein $R_3$, $W_1$, and m' are as defined in claim 1.

26. A dyeing composition comprising, in a medium suitable for dyeing of keratin fibers, a direct dye chosen from at least one compound chosen from those of formula (I), (II) and (III) below, acid addition salts, solvates, and mixtures thereof, wherein in the compounds of formulae (I), (II), and (III), the formula members attached to each side of the linker L are either compositionally different or positionally different such that the compounds as a whole are dissymmetrical:

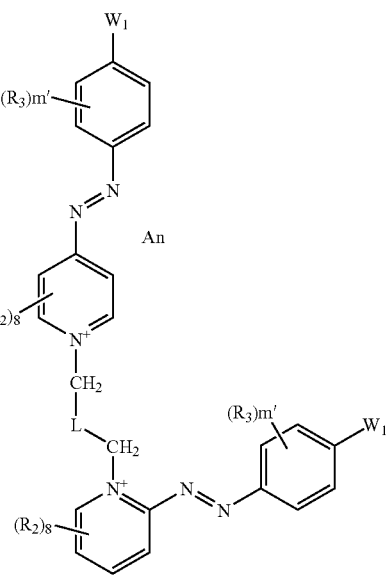

(I)

-continued

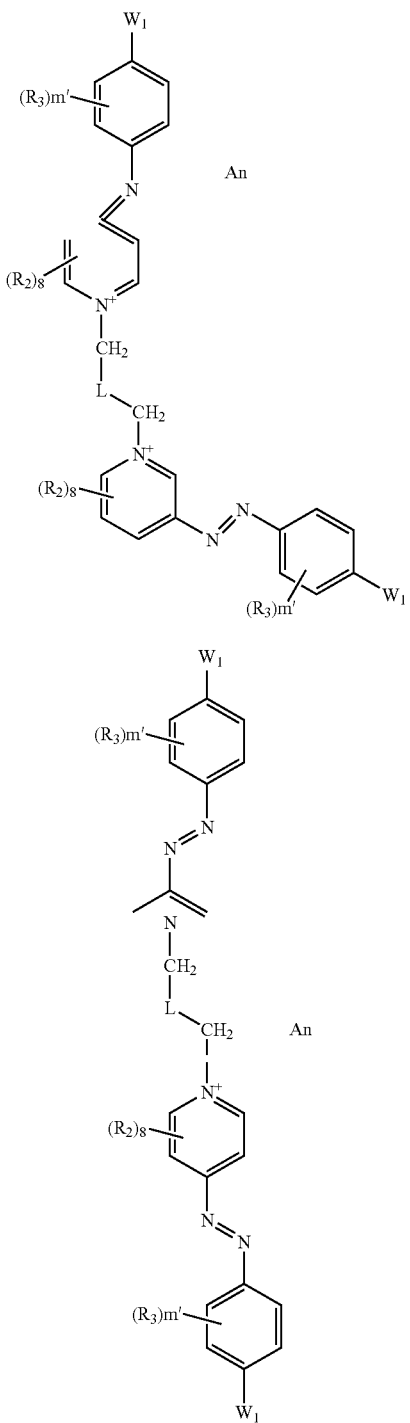

wherein:
the radicals $R_2$, which are identical or different, independently of one another are chosen from:
$C_1$-$C_{16}$ alkyl radicals optionally interrupted by at least one heteroatom and/or at least one group containing at least one heteroatom, said alkyl radicals being optionally substituted by at least one group chosen from hydroxyl, $C_1$-$C_2$ alkoxy, $C_2$-$C_4$ (poly)hydroxy-alkoxy, amino, $C_1$-$C_2$ (di)alkylamino, thio (—SH), $C_1$-$C_4$ thioalkyl, $C_1$-$C_4$ alkylsulphinyl, and $C_1$-$C_4$ alkylsulphonyl groups;
hydroxyl groups;
$C_1$-$C_4$ alkoxy groups;
$C_2$-$C_4$ (poly)hydroxyalkoxy groups;
a $C_2$-$C_4$ (poly)hydroxyalkylamino groups;
alkoxycarbonyl groups (RO—CO—) wherein R is a $C_1$-$C_4$ alkyl radical;
alkylcarbonyloxy groups (RCO—O—) wherein R is a $C_1$-$C_4$ alkyl radical;
alkylcarbonyl groups (R—CO—) wherein R is a $C_1$-$C_4$ alkyl radical;
amino groups;
amino groups substituted by one or two identical or different $C_1$-$C_4$ alkyl radicals optionally carrying at least one hydroxyl group, wherein the two alkyl radicals may optionally form, with the nitrogen atom to which they are attached, a heterocycle containing 1 to 3 heteroatoms chosen from N, O and S, and containing 5 to 7 ring members, wherein said heterocycle is saturated or unsaturated, aromatic or non-aromatic and is optionally substituted;
alkylcarbonylamino groups (RCO—NR'—) wherein R is a $C_1$-$C_4$ alkyl radical and R' is chosen from hydrogen and a $C_1$-$C_4$ alkyl radical;
aminocarbonyl groups ($(R)_2$N—CO—) wherein radicals R independently of one another are chosen from a hydrogen atom and a $C_1$-$C_4$ alkyl radical;
ureido groups (N(R)$_2$—CO—NR'—) wherein radicals R and R' independently of one another are chosen from a hydrogen atom and a $C_1$-$C_4$ alkyl radical;
aminosulphonyl groups ($(R)_2$N—SO$_2$—) wherein radicals R independently of one another are chosen from a hydrogen atom and a $C_1$-$C_4$ alkyl radical;
alkylsulphonylamino groups (RSO$_2$-NR'—) wherein R is a $C_1$-$C_4$ alkyl radical and R' is chosen from a hydrogen atom and a $C_1$-$C_4$ alkyl radical;
optionally substituted aryl radicals;
optionally substituted ($C_1$-$C_4$)alkylaryl radicals;
alkylsulphinyl groups (R—SO—) wherein R is a $C_1$-$C_4$ alkyl radical;
alkylsulphonyl groups (R—SO$_2$—) wherein R is a $C_1$-$C_4$ alkyl radical;
nitro groups;
cyano groups;
halogen atoms;
thio groups (HS—);
alkylthio groups (RS—) wherein R is an optionally substituted $C_1$-$C_4$ alkyl radical; and
when e is 2, for each of the formulae (I), (II), and (III), two radicals $R_2$ may optionally form, with the carbon atoms to which they are attached, a secondary ring, aromatic or non-aromatic, containing 5 or 6 ring members, which is optionally substituted by at least one identical or different group chosen from hydroxyl, $C_1$-$C_4$ alkyl, $C_1$-$C_4$ alkoxy, $C_2$-$C_4$ (poly)hydroxyalkoxy, amino, and amino substituted by one or two identical or different $C_1$-$C_4$alkyl radicals which optionally carry at least one group chosen from hydroxyl and methylcarbonylamino groups;
e is an integer ranging from 0 to 4; when e is less than 4, the unsubstituted carbon atom(s) of the heterocycle of the formulae (I), (II), and (III) carry a hydrogen atom;
the radicals $R_3$, from formulae (I), (II), and (III), which are identical or different, independently of one another are chosen from:

optionally substituted $C_1$-$C_{16}$ alkyl radicals optionally interrupted by at least one heteroatom or by at least one group containing at least one heteroatom;

hydroxyl groups;

$C_1$-$C_4$ alkoxy groups;

$C_2$-$C_4$ (mono) or (poly)hydroxyalkoxy groups;

alkoxycarbonyl groups (RO—CO—) wherein R is a $C_1$-$C_4$ alkyl radical;

alkylcarbonyloxy groups (RCO—O—) wherein R is a $C_1$-$C_4$ alkyl radical;

alkylcarbonyl groups (R—CO—) wherein R is a $C_1$-$C_4$ alkyl radical;

amino groups;

amino groups substituted by one or two identical or different $C_1$-$C_4$ alkyl radicals optionally carrying at least one group chosen from hydroxyl and $C_1$-$C_4$ alkoxy groups; wherein the two alkyl radicals may optionally form, with the nitrogen atom to which they are attached, a heterocycle containing 1 to 3 heteroatoms chosen from N, O and S, containing 5 to 7 ring members, and which is saturated or unsaturated, aromatic or non-aromatic and is optionally substituted;

alkylcarbonylamino groups (RCO—NR'—) wherein the radical R is a $C_1$-$C_4$ alkyl radical and the radical R' is chosen from a hydrogen atom and a $C_1$-$C_4$ alkyl radical;

aminocarbonyl groups ((R)$_2$N—CO—) wherein radicals R independently of one another are chosen from a hydrogen atom and a $C_1$-$C_4$ alkyl radical;

ureido groups (N(R)$_2$—CO—NR'—) wherein radicals R and R' independently of one another are chosen from a hydrogen atom and a $C_1$-$C_4$ alkyl radical;

aminosulphonyl groups ((R)$_2$N—SO$_2$—) wherein radicals R independently of one another are chosen from a hydrogen atom and a $C_1$-$C_4$ alkyl radical;

alkylsulphonylamino groups (RSO$_2$—NR'—) wherein radicals R and R' independently of one another are chosen from a hydrogen atom and a $C_1$-$C_4$ alkyl radical;

thio groups (HS—);

alkylthio groups (RS—) wherein R is a $C_1$-$C_4$ alkyl radical;

alkylsulphinyl groups (R—SO—) wherein R is a $C_1$-$C_4$ alkyl radical;

alkylsulphonyl groups (R—SO$_2$—) wherein R is a $C_1$-$C_4$ alkyl radical;

nitro groups;

cyano groups;

halogen atoms; and when m' greater than or equal to 2, two adjacent radicals $R_3$ may form, with the carbon atoms to which they are attached, a secondary ring, aromatic or non-aromatic containing 6 ring members, which is optionally substituted by at least one identical or different group chosen from: hydroxyl, —NR$_4$—Ph, —NR$_4$—Ph—NR$_5$R$_6$, —NR$_4$—Ph—OR$_7$, $C_1$-$C_4$ alkyl, $C_1$-$C_4$ alkoxy, $C_2$-$C_4$ (poly)hydroxyalkoxy, $C_1$-$C_4$ alkylcarbonylamino, amino, and amino substituted by one or two identical or different $C_1$-$C_4$ alkyl radicals which optionally carry at least one hydroxyl group;

m' is an integer from 0 to 4; when m' is less than 4, then the unsubstituted carbon atom(s) of the aromatic ring of the formulae (I), (II), and (III) carry a hydrogen atom;

the $W_1$ groups of the formulae (I), (II), and (III), which are identical or different, independently of one another, are chosen from:

hydrogen atoms;

halogen atoms chosen from bromine, chlorine and fluorine; and a group chosen from —NR$_5$R$_6$, OR$_7$, —NR$_4$—Ph—NR$_5$R$_6$, —NR$_4$—Ph—OR$_7$, —O—Ph—OR$_7$, and —O—Ph—NR$_5$R$_6$ groups, wherein:

$R_4$ and $R_7$, which may be identical or different, are independently chosen from a hydrogen atom, an optionally substituted $C_1$-$C_{20}$ alkyl radical, an optionally substituted aryl or aralkyl radical and an optionally substituted phenyl radical;

$R_5$ and $R_6$, which are identical or different, are chosen from a hydrogen atom, an optionally substituted $C_1$-$C_{20}$ alkyl radical, an optionally substituted phenyl radical, an optionally substituted aryl or aralkyl radical and an alkylcarbonyl radical (R—CO—) wherein R is a $C_1$-$C_4$ alkyl radical; and $R_5$ and $R_6$ may optionally form, with the nitrogen atom to which they are attached, a heterocycle containing 1 to 3 heteroatoms, chosen from N, O and S, and containing 5 to 7 ring members, which is saturated or unsaturated, aromatic or non-aromatic and is optionally substituted; or $R_5$ and $R_6$ may optionally form, with the carbon atom of the aromatic ring that is optionally substituted by a hydroxyl and adjacent to that to which —NR$_5$R$_6$ is attached, a 5- or 6-membered saturated or unsaturated heterocycle;

Ph is an optionally substituted phenyl radical;

L is chosen from a cationic linker and a non-cationic linker;

An is chosen from at least one identical or different cosmetically acceptable anions which ensure the electroneutrality of the compounds of formulas (I), (II) and (III).

27. The dyeing composition of claim 26, wherein said at least one compound of formula (I), (II) or (III) or of each of said compounds of formula (I), (II) or (III), is present in an amount ranging from 0.001% to 20% by weight relative to the total weight of the dyeing composition.

28. The dyeing composition of claim 27, wherein said at least one compound or each of said compounds of formula (I), (II) or (III) is present in an amount ranging from 0.02% to 10% by weight, relative to the total weight of the dyeing composition.

29. The dyeing composition of claim 26, wherein said dyeing composition further comprises at least one additional direct dye, and/or at least one oxidation base optionally in combination with at least one coupler.

30. The dyeing composition of claim 29, wherein said at least one additional direct dye is a cationic or nonionic dye chosen from nitrobenzene, azo, azomethine, methine, tetraazapentamethine, anthraquinone, naphthoquinone, benzoquinone, phenothiazine, indigoid, xanthene, phenanthridine, and phthalocyanine dyes, dyes derived from triarylmethane, and natural dyes, and mixtures thereof.

31. The dyeing composition of claim 29, wherein said at least one oxidation base is chosen from p-phenylenediamines, bisphenylalkylenediamines, o-aminophenols, p-aminophenols and heterocyclic bases.

32. The dyeing composition of claim 29, wherein said at least one coupler is chosen from m-aminophenols, m-phenylenediamines, m-diphenols, naphthalenic couplers, heterocyclic couplers, their acid addition salts, and mixtures thereof.

33. The dyeing composition of claim 26, wherein said dyeing composition further comprises at least one oxidizing agent.

34. A method of coloring keratin fibers, comprising contacting said fibers, which may be dry or wet, with a dyeing composition for a time sufficient to give a desired color, wherein the dyeing composition comprises, in a medium, suitable for dyeing keratin fibers, at least one direct dye chosen from those of formula (I), (II) and (III) below, acid addition salts thereof solvates thereof, and mixtures thereof wherein in the compounds of formulae (I), (II), and (III), the formula members attached to each side of the linker L are either compositionally different or positionally different such that the compounds as a whole are dissymmetrical:

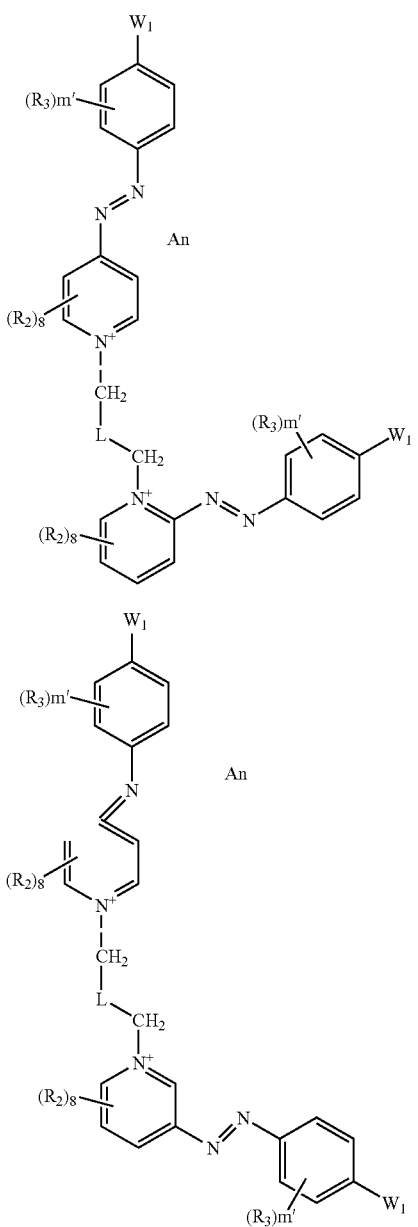

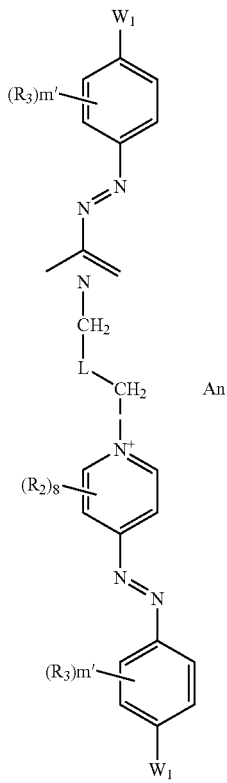

wherein:
the radicals $R_2$, which are identical or different, independently of one another are chosen from:
$C_1$-$C_{16}$ alkyl radicals optionally interrupted by at least one heteroatom and/or at least one group containing at least one heteroatom, said alkyl radicals being optionally substituted by at least one group chosen from hydroxyl, $C_1$-$C_2$ alkoxy, $C_2$-$C_4$ (poly)hydroxyalkoxy, amino, $C_1$-$C_2$ (di)alkylamino, thio (—SH), $C_1$-$C_4$ thioalkyl, $C_1$-$C_4$ alkylsulphinyl, and $C_1$-$C_4$ alkylsulphonyl groups;
hydroxyl groups;
$C_1$-$C_4$ alkoxy groups;
$C_2$-$C_4$ (poly)hydroxyalkoxy groups;
$C_2$-$C_4$ (poly)hydroxyalkylamino groups;
alkoxycarbonyl groups (RO—CO—) wherein R is a $C_1$-$C_4$ alkyl radical;
alkylcarbonyloxy groups (RCO—O—) wherein R is a $C_1$-$C_4$ alkyl radical;
alkylcarbonyl groups (R—CO—) wherein R is a $C_1$-$C_4$ alkyl radical;
amino groups;
amino groups substituted by one or two identical or different $C_1$-$C_4$ alkyl radicals optionally carrying at least one hydroxyl group, wherein the two alkyl radicals may optionally form, with the nitrogen atom to which they are attached, a heterocycle containing 1 to 3 heteroatoms chosen from N, O and S, and containing 5 to 7 ring members, wherein said heterocycle is saturated or unsaturated, aromatic or non-aromatic and is optionally substituted;

alkylcarbonylamino groups (RCO—NR'—) wherein R is a $C_1$-$C_4$ alkyl radical and R' is chosen from hydrogen and a $C_1$-$C_4$ alkyl radical;

aminocarbonyl groups ((R)$_2$N—CO—) wherein radicals R independently of one another are chosen from a hydrogen atom and a $C_1$-$C_4$ alkyl radical;

ureido groups (N(R)$_2$—CO—NR'—) wherein radicals R and R' independently of one another are chosen from a hydrogen atom and a $C_1$-$C_4$ alkyl radical;

aminosulphonyl groups ((R)$_2$N—SO$_2$—) wherein radicals R independently of one another are chosen from a hydrogen atom and a $C_1$-$C_4$ alkyl radical;

alkylsulphonylamino groups (RSO$_2$—NR'—) wherein R is a $C_1$-$C_4$ alkyl radical and R' is chosen from a hydrogen atom and a $C_1$-$C_4$ alkyl radical;

optionally substituted aryl radicals;

optionally substituted ($C_1$-$C_4$)alkylaryl radicals;

alkylsulphinyl groups (R—SO—) wherein R is a $C_1$-$C_4$ alkyl radical;

alkylsulphonyl groups (R—SO$_2$—) wherein R is a $C_1$-$C_4$ alkyl radical;

nitro groups;

cyano groups;

halogen atoms;

thio groups (HS—);

alkylthio groups (RS—) wherein R is an optionally substituted $C_1$-$C_4$ alkyl radical; and when e is 2, for each of the formulae (I), (II), and (III), two radicals R$_2$ may optionally form, with the carbon atoms to which they are attached, a secondary ring, aromatic or non-aromatic, containing 5 or 6 ring members, which is optionally substituted by at least one identical or different group chosen from hydroxyl, $C_1$-$C_4$ alkyl, $C_1$-$C_4$ alkoxy, $C_2$-$C_4$ (poly)hydroxyalkoxy, amino, and amino substituted by one or two identical or different $C_1$-$C_4$ alkyl radicals which optionally carry at least one group chosen from hydroxyl and methylcarbonylamino groups;

e is an integer ranging from 0 to 4; when e is less than 4, the unsubstituted carbon atom(s) of the heterocycle of the formulae (I), (II), and (III) carry a hydrogen atom;

the radicals R$_3$, from formulae (I), (II), and (III), which are identical or different, independently of one another are chosen from:

optionally substituted $C_1$-$C_{16}$ alkyl radicals optionally interrupted by at least one heteroatom or by at least one group containing at least one heteroatom;

hydroxyl groups;

$C_1$-$C_4$ alkoxy groups;

$C_2$-$C_4$ (mono) or (poly)hydroxyalkoxy groups;

alkoxycarbonyl groups (RO—CO—) wherein R is a $C_1$-$C_4$ alkyl radical;

alkylcarbonyloxy groups (RCO—O—) wherein R is a $C_1$-$C_4$ alkyl radical;

alkylcarbonyl groups (R—CO—) wherein R is a $C_1$-$C_4$ alkyl radical;

amino groups;

amino groups substituted by one or two identical or different $C_1$-$C_4$ alkyl radicals optionally carrying at least one group chosen from hydroxyl and $C_1$-$C_4$ alkoxy groups; wherein the two alkyl radicals may optionally form, with the nitrogen atom to which they are attached, a heterocycle containing 1 to 3 heteroatoms chosen from N, O and S, containing 5 to 7 ring members, and which is saturated or unsaturated, aromatic or non-aromatic and is optionally substituted;

alkylcarbonylamino groups (RCO—NR'—) wherein the radical R is a $C_1$-$C_4$ alkyl radical and the radical R' is chosen from a hydrogen atom and a $C_1$-$C_4$ alkyl radical;

aminocarbonyl groups ((R)$_2$N—CO—) wherein radicals R independently of one another are chosen from a hydrogen atom and a $C_1$-$C_4$ alkyl radical;

ureido groups (N(R)$_2$-CO—NR'—) wherein radicals R and R' independently of one another are chosen from a hydrogen atom and a $C_1$-$C_4$ alkyl radical;

aminosulphonyl groups ((R)$_2$N—SO$_2$—) wherein radicals R independently of one another are chosen from a hydrogen atom and a $C_1$-$C_4$ alkyl radical;

alkylsulphonylamino groups (RSO$_2$—NR'—) wherein radicals R and R' independently of one another are chosen from a hydrogen atom and a $C_1$-$C_4$ alkyl radical;

thio groups (HS—);

alkylthio groups (RS—) wherein R is a $C_1$-$C_4$ alkyl radical;

alkylsulphinyl groups (R—SO—) wherein R is a $C_1$-$C_4$ alkyl radical;

alkylsulphonyl groups (R—SO$_2$—) wherein R is a $C_1$-$C_4$ alkyl radical;

nitro groups;

cyano groups;

halogen atoms; and when m' is greater than or equal to 2, two adjacent radicals R$_3$ may form, with the carbon atoms to which they are attached, a secondary ring, aromatic or non-aromatic containing 6 ring members, which is optionally substituted by at least one identical or different group chosen from: hydroxyl, —NR$_4$—Ph, —NR$_4$—Ph—NR$_5$R$_6$, —NR$_4$—Ph—OR$_7$, $C_1$-$C_4$ alkyl, $C_1$-$C_4$ alkoxy, $C_2$-$C_4$ (poly)hydroxyalkoxy, $C_1$-$C_4$ alkylcarbonylamino, amino, and amino substituted by one or two identical or different $C_1$-$C_4$ alkyl radicals which optionally carry at least one hydroxyl group;

m' is an integer from 0 to 4; when m' is less than 4, then the unsubstituted carbon atom(s) of the aromatic ring of the formulae (I), (II), and (III) carry a hydrogen atom;

the W$_1$ groups of the formulae (I), (II), and (III), which are identical or different, independently of one another, are chosen from:

hydrogen atoms;

halogen atoms chosen from bromine, chlorine and fluorine; and a group chosen from —NR$_5$R$_6$, OR$_7$, —NR$_4$—Ph—NR$_5$R$_6$, —NR$_4$—Ph—OR$_7$, —O—Ph—OR$_7$ and —O—Ph—NR$_5$R$_6$ groups, wherein:

R$_4$ and R$_7$, which may be identical or different, are independently chosen from a hydrogen atom, an optionally substituted $C_1$-$C_{20}$ alkyl radical, an optionally substituted aryl or aralkyl radical and an optionally substituted phenyl radical;

$R_5$ and $R_6$, which are identical or different, are chosen from a hydrogen atom, an optionally substituted $C_1$-$C_{20}$ alkyl radical, an optionally substituted phenyl radical, an optionally substituted aryl or aralkyl radical and an alkylcarbonyl radical (R—CO—) wherein R is a $C_1$-$C_4$ alkyl radical; and $R_5$ and $R_6$ may optionally form, with the nitrogen atom to which they are attached, a heterocycle containing 1 to 3 heteroatoms, chosen from N, O and S, and containing 5 to 7 ring members, which is saturated or unsaturated, aromatic or non-aromatic and is optionally substituted; or $R_5$ and $R_6$ may optionally form, with the carbon atom of the aromatic ring that is optionally substituted by a hydroxyl and adjacent to that to which —$NR_5R_6$ is attached, a 5- or 6-membered saturated or unsaturated heterocycle;

Ph is an optionally substituted phenyl radical;

L is chosen from a cationic linker and a non-cationic linker;

An is chosen from at least one identical or different cosmetically acceptable anions which ensure the electroneutrality of the compounds of formulas (I), (II) and (III).

35. A device comprising a plurality of compartments, in which a first compartment comprises a dyeing composition and a second compartment comprises an oxidizing composition, wherein said dyeing composition comprises, in a medium suitable for dyeing keratin fibers, at least one direct dye chosen from those of formula (I), (II) and (III) below, acid addition salts, solvates, and mixtures thereof, wherein in the compounds of formulae (I), (II), and (III), the formula members attached to each side of the linker L are either compositionally different or positionally different such that the compounds as a whole are dissymmetrical:

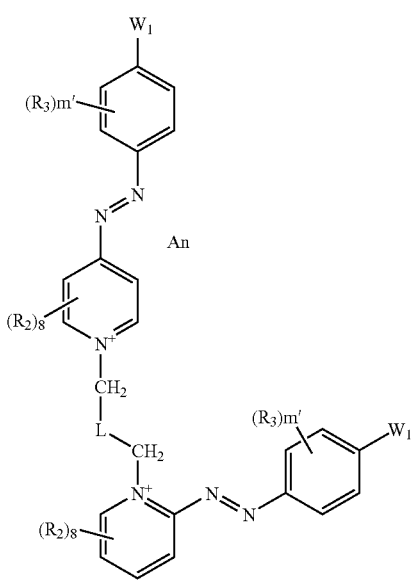

(I)

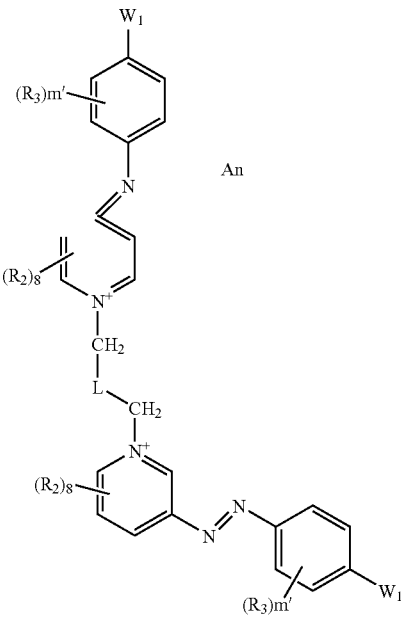

(II)

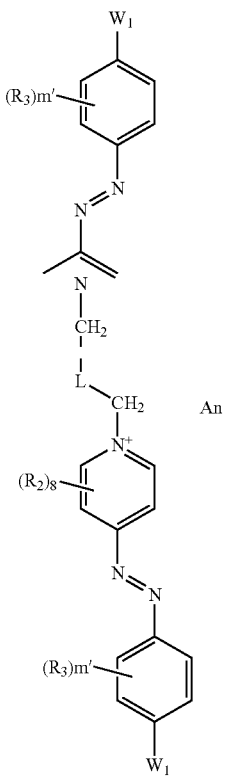

(III)

wherein:

the radicals $R_2$, which are identical or different, independently of one another are chosen from:

$C_1$-$C_{16}$ alkyl radicals optionally interrupted by at least one heteroatom and/or at least one group containing at least one heteroatom, said alkyl radicals being optionally substituted by at least one group chosen from hydroxyl, $C_1$-$C_2$ alkoxy, $C_2$-$C_4$ (poly)hydroxyalkoxy, amino, C₁-C₂ (di)alkylamino, thio (—SH), $C_1$-$C_4$ thioalkyl, $C_1$-$C_4$ alkylsulphinyl, and $C_1$-$C_4$ alkylsulphonyl groups;

hydroxyl groups;

$C_1$-$C_4$ alkoxy groups;

$C_2$-$C_4$ (poly)hydroxyalkoxy groups;

$C_2$-$C_4$ (poly)hydroxyalkylamino groups;

alkoxycarbonyl groups (RO—CO—) wherein R is a $C_1$-$C_4$ alkyl radical;

alkylcarbonyloxy groups (RCO—O—) wherein R is a $C_1$-$C_4$ alkyl radical;

alkylcarbonyl groups (R—CO—) wherein R is a $C_1$-$C_4$ alkyl radical;

amino groups;

amino groups substituted by one or two identical or different $C_1$-$C_4$ alkyl radicals optionally carrying at least one hydroxyl group, wherein the two alkyl radicals may optionally form, with the nitrogen atom to which they are attached, a heterocycle containing 1 to 3 heteroatoms chosen from N, O and S, and containing 5 to 7 ring members, wherein said heterocycle is saturated or unsaturated, aromatic or non-aromatic and is optionally substituted;

alkylcarbonylamino groups (RCO—NR'—) wherein R is a $C_1$-$C_4$ alkyl radical and R' is chosen from hydrogen and a $C_1$-$C_4$ alkyl radical;

aminocarbonyl groups ((R)₂N—CO—) wherein radicals R independently of one another are chosen from a hydrogen atom and a $C_1$-$C_4$ alkyl radical;

ureido groups (N(R)₂—CO—NR'—) wherein radicals R and R' independently of one another are chosen from a hydrogen atom and a $C_1$-$C_4$ alkyl radical;

aminosulphonyl groups ((R)₂N—SO₂—) wherein radicals R independently of one another are chosen from a hydrogen atom and a $C_1$-$C_4$ alkyl radical;

alkylsulphonylamino groups (RSO₂—NR'—) wherein R is a $C_1$-$C_4$ alkyl radical and R' is chosen from a hydrogen atom and a $C_1$-$C_4$ alkyl radical;

optionally substituted aryl radicals;

optionally substituted ($C_1$-$C_4$)alkylaryl radicals;

alkylsulphinyl groups (R—SO—) wherein R is a $C_1$-$C_4$ alkyl radical;

alkylsulphonyl groups (R—SO₂—) wherein R is a $C_1$-$C_4$ alkyl radical;

nitro groups;

cyano groups;

halogen atoms;

thio groups (HS—);

alkylthio groups (RS—) wherein R is an optionally substituted $C_1$-$C_4$ alkyl radical; and when e is 2, for each of the formulae (I), (II), and (III), two radicals R₂ may optionally form, with the carbon atoms to which they are attached, a secondary ring, aromatic or non-aromatic, containing 5 or 6 ring members, which is optionally substituted by at least one identical or different group chosen from hydroxyl, $C_1$-$C_4$ alkyl, $C_1$-$C_4$ alkoxy, $C_2$-$C_4$ (poly)hydroxyalkoxy, amino, and amino substituted by one or two identical or different $C_1$-$C_4$ alkyl radicals which optionally carry at least one group chosen from hydroxyl and methylcarbonylamino groups;

e is an integer ranging from 0 to 4; when e is less than 4, the unsubstituted carbon atom(s) of the heterocycle of the formulae (I), (II), and (III) carry a hydrogen atom;

the radicals R₃, from formulae (I), (II), and (III), which are identical or different, independently of one another are chosen from:

optionally substituted $C_1$-$C_{16}$ alkyl radicals optionally interrupted by at least one heteroatom or by at least one group containing at least one heteroatom;

hydroxyl groups;

$C_1$-$C_4$ alkoxy groups;

$C_2$-$C_4$ (mono) or (poly)hydroxyalkoxy groups;

alkoxycarbonyl groups (RO—CO—) wherein R is a $C_1$-$C_4$ alkyl radical;

alkylcarbonyloxy groups (RCO—O—) wherein R is a $C_1$-$C_4$ alkyl radical;

alkylcarbonyl groups (R—CO—) wherein R is a $C_1$-$C_4$ alkyl radical;

amino groups;

amino groups substituted by one or two identical or different $C_1$-$C_4$ alkyl radicals optionally carrying at least one group chosen from hydroxyl and $C_1$-$C_4$ alkoxy groups; wherein the two alkyl radicals may optionally form, with the nitrogen atom to which they are attached, a heterocycle containing 1 to 3 heteroatoms chosen from N, O and S, containing 5 to 7 ring members, and which is saturated or unsaturated, aromatic or non-aromatic and is optionally substituted;

alkylcarbonylamino groups (RCO—NR'—) wherein the radical R is a $C_1$-$C_4$ alkyl radical and the radical R' is chosen from a hydrogen atom and a $C_1$-$C_4$ alkyl radical;

aminocarbonyl groups ((R)₂N—CO—) wherein radicals R independently of one another are chosen from a hydrogen atom and a $C_1$-$C_4$ alkyl radical;

ureido groups (N(R)₂—CO—NR'—) wherein radicals R and R' independently of one another are chosen from a hydrogen atom and a $C_1$-$C_4$ alkyl radical;

aminosulphonyl groups ((R)₂N—SO₂—) wherein radicals R independently of one another are chosen from a hydrogen atom and a $C_1$-$C_4$ alkyl radical;

alkylsulphonylamino groups (RSO₂—NR'—) wherein radicals R and R' independently of one another are chosen from a hydrogen atom and a $C_1$-$C_4$ alkyl radical;

thio groups (HS—);

alkylthio groups (RS—) wherein R is a $C_1$-$C_4$ alkyl radical;

alkylsulphinyl groups (R—SO—) wherein R is a $C_1$-$C_4$ alkyl radical;

alkylsulphonyl groups (R—SO₂—) wherein R is a $C_1$-$C_4$ alkyl radical;

nitro groups;

cyano groups;

halogen atoms; and when m' greater than or equal to 2, two adjacent radicals R₃ may form, with the carbon atoms to which they are attached, a secondary ring, aromatic or non-aromatic containing 6 ring members, which is optionally substituted by at least one identical or different group chosen from: hydroxyl, —NR₄—Ph, —NR₄—Ph—NR₅R₆, —NR₄—Ph—OR₇, $C_1$-$C_4$ alkyl, $C_1$-$C_4$ alkoxy, $C_2$-$C_4$ (poly)hydroxyalkoxy, $C_1$-$C_4$ alkylcarbonylamino, amino, and amino substituted by one or two identical or different $C_1$-$C_4$ alkyl radicals which optionally carry at least one hydroxyl group;

m' is an integer from 0 to 4; when m' is less than 4, then the unsubstituted carbon atom(s) of the aromatic ring of the formulae (I), (II), and (III) carry a hydrogen atom;

the $W_1$ groups of the formulae (I), (II), and (III), which are identical or different, independently of one another, are chosen from:

hydrogen atoms;

halogen atoms chosen from bromine, chlorine and fluorine; and a group chosen from $-NR_5R_6$, $OR_7$, $-NR_4-Ph-NR_5R_6$, $-NR_4-Ph-OR_7$, $-O-Ph-OR_7$ and $-O-Ph-NR_5R_6$ groups, wherein:

$R_4$ and $R_7$, which may be identical or different, are independently chosen from a hydrogen atom, an optionally substituted $C_1$-$C_{20}$ alkyl radical, an optionally substituted aryl or aralkyl radical and an optionally substituted phenyl radical;

$R_5$ and $R_6$, which are identical or different, are chosen from a hydrogen atom, an optionally substituted $C_1$-$C_{20}$ alkyl radical, an optionally substituted phenyl radical, an optionally substituted aryl or aralkyl radical and an alkylcarbonyl radical (R—CO—) wherein R is a $C_1$-$C_4$ alkyl radical; and $R_5$ and $R_6$ may optionally form, with the nitrogen atom to which they are attached, a heterocycle containing 1 to 3 heteroatoms, chosen from N, O and S, and containing 5 to 7 ring members, which is saturated or unsaturated, aromatic or non-aromatic and is optionally substituted; or $R_5$ and $R_6$ may optionally form, with the carbon atom of the aromatic ring that is optionally substituted by a hydroxyl and adjacent to that to which $-NR_5R_6$ is attached, a 5- or 6-membered saturated or unsaturated heterocycle;

Ph is an optionally substituted phenyl radical;

L is chosen from a cationic linker and a non-cationic linker;

An is chosen from at least one identical or different cosmetically acceptable anions which ensure the electroneutrality of the compounds of formulas (I), (II) and (III).

* * * * *

UNITED STATES PATENT AND TRADEMARK OFFICE
CERTIFICATE OF CORRECTION

PATENT NO. : 7,288,639 B2
APPLICATION NO. : 11/300314
DATED : October 30, 2007
INVENTOR(S) : Hervé David et al.

All structures that include "$(R_2)_8$" should read -- $(R_2)e$ --, as shown on the attached sheets.

Claim 13, col. 48, line 63, "awl" should read -- aryl --.

Claim 14, col. 49, line 1, "awl" should read -- aryl --.

Claim 21, col. 49, line 63, "and for" should read -- and/or --.

Signed and Sealed this

First Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,288,639 B2
APPLICATION NO. : 11/300314
DATED : October 30, 2007
INVENTOR(S) : Hervé David et al.

It is certified that error appears in the above-identified patent and that said Letters Patent is hereby corrected as shown below:

Claim 1, col. 43, line 1-34,

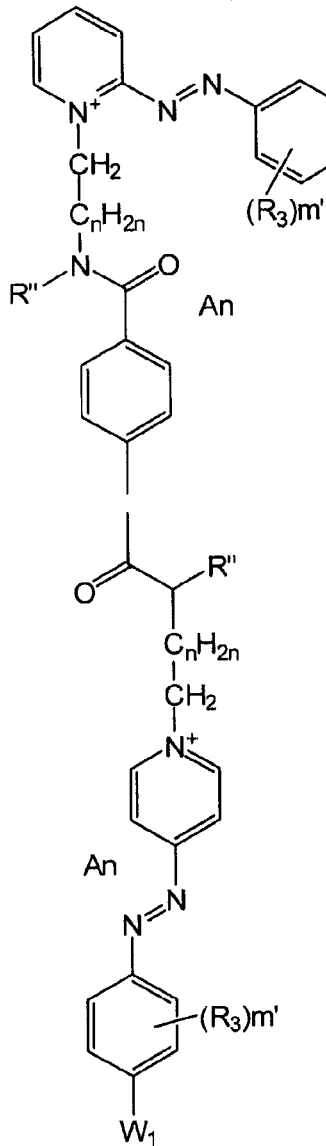

R" = H, Me
n = integer between 1 and should read

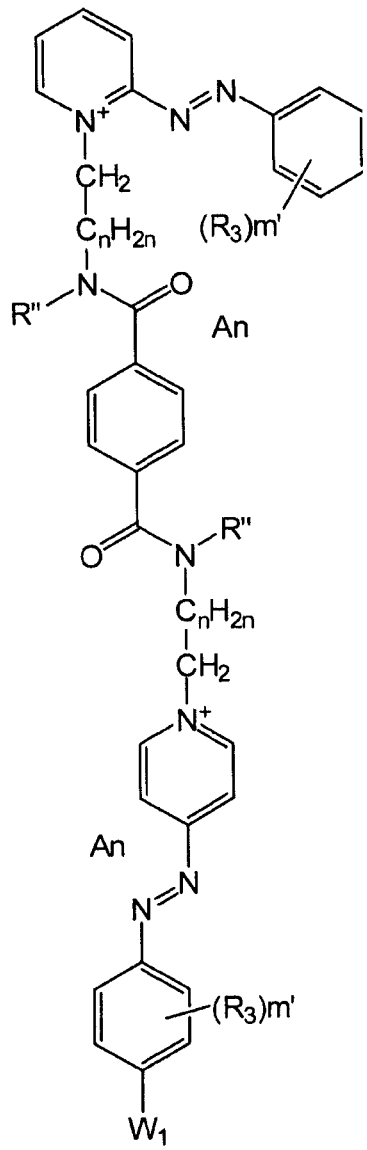

R" = H, Me
n = integer between 1 and

UNITED STATES PATENT AND TRADEMARK OFFICE
CERTIFICATE OF CORRECTION

PATENT NO.       : 7,288,639 B2                                  Page 3 of 4
APPLICATION NO. : 11/300314
DATED            : October 30, 2007
INVENTOR(S)      : Hervé David et al.

It is certified that error appears in the above-identified patent and that said Letters Patent is hereby corrected as shown below:

Claim 1, col. 43, line 1-34,

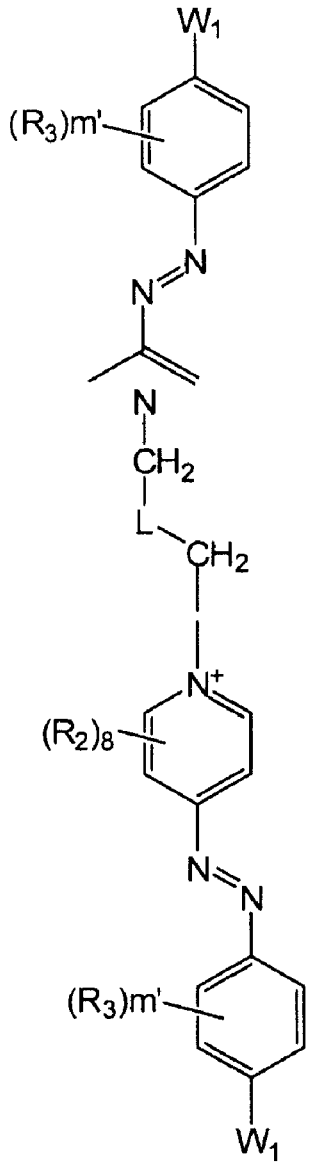 An     should read     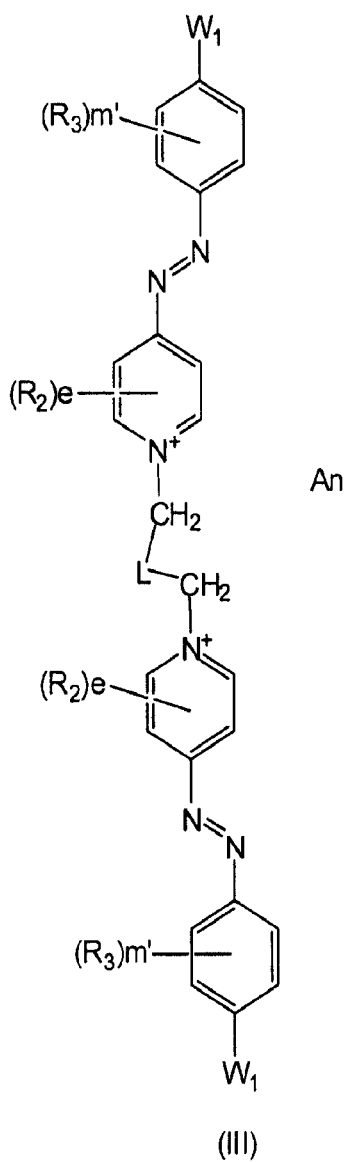

UNITED STATES PATENT AND TRADEMARK OFFICE
CERTIFICATE OF CORRECTION

PATENT NO. : 7,288,639 B2
APPLICATION NO. : 11/300314
DATED : October 30, 2007
INVENTOR(S) : Hervé David et al.

It is certified that error appears in the above-identified patent and that said Letters Patent is hereby corrected as shown below:

Claim 1, col. 43, line 1-34,

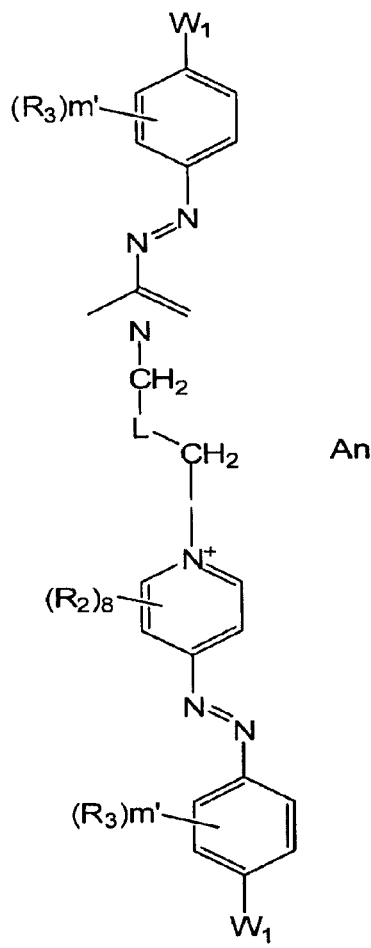 should read 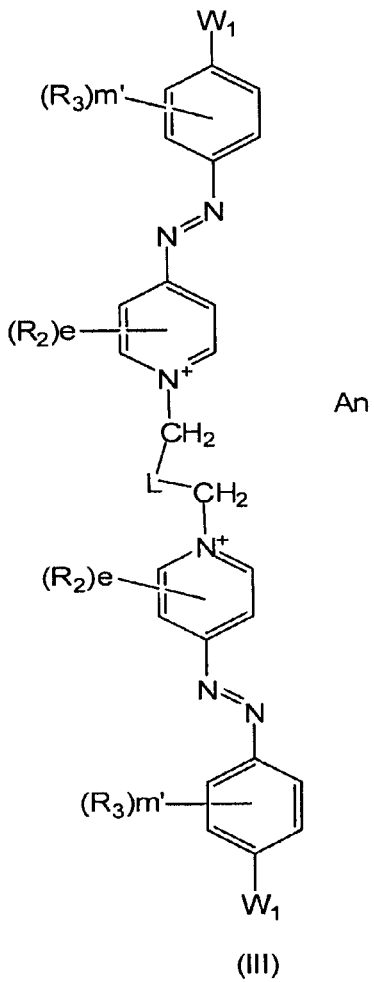

(III)